United States Patent
Falkenstein et al.

(10) Patent No.: US 8,226,649 B2
(45) Date of Patent: * Jul. 24, 2012

(54) BIPOLAR ELECTROSURGICAL SCISSORS

(75) Inventors: Zoran Falkenstein, Rancho Santa Margarita, CA (US); Blaze Brown, Anaheim, CA (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1028 days.

This patent is subject to a terminal disclaimer.

(21) Appl. No.: 12/183,970

(22) Filed: Jul. 31, 2008

(65) Prior Publication Data

US 2009/0005779 A1 Jan. 1, 2009

Related U.S. Application Data

(63) Continuation of application No. 11/460,292, filed on Jul. 27, 2006, now Pat. No. 7,419,490.

(51) Int. Cl.
*A61B 18/14* (2006.01)
(52) U.S. Cl. .......................................... 606/50; 606/45
(58) Field of Classification Search .................... 606/40, 606/41, 45–52

See application file for complete search history.

(56) References Cited

U.S. PATENT DOCUMENTS

| | | |
|---|---|---|
| 3,460,539 A | 8/1969 | Anhalt, Sr. |
| 3,987,795 A | 10/1976 | Morrison |
| 4,202,337 A | 5/1980 | Hren et al. |
| 4,228,800 A | 10/1980 | Degler, Jr. et al. |
| 4,850,353 A | 7/1989 | Stasz et al. |
| 5,324,289 A * | 6/1994 | Eggers ............................. 606/48 |
| 5,443,463 A | 8/1995 | Stern et al. |
| 5,496,312 A | 3/1996 | Klicek |
| 5,540,685 A * | 7/1996 | Parins et al. .................... 606/51 |
| 5,573,534 A | 11/1996 | Stone |

(Continued)

FOREIGN PATENT DOCUMENTS

JP 2000 005188 A 1/2000

OTHER PUBLICATIONS

International Bureau of WIPO, The International Preliminary Report on Patentability for International Application No. PCT/US07/073045, mailed Feb. 5, 2009.

(Continued)

*Primary Examiner* — Michael Peffley
(74) *Attorney, Agent, or Firm* — Patrick Y. Ikehara; John F. Heal; David G. Majdali

(57) ABSTRACT

Bipolar electrosurgical scissors for treating biological tissue include first and second scissor blades. A shearing surface and cutting edge of each blade is electrically neutral. The scissors include a pair of electrical connections for receiving electrical currents of opposing polarities. Each blade includes at least one first electrode and at least one second electrode positioned on a surface opposite the shearing surface. The at least one first electrode on the first blade and the at least one second electrode on the second blade are coupled to the first electrical connection. The at least one second electrode on the first blade and the at least one first electrode on the second blade are coupled to the second electrical connection. In a first energized state, the electrical connections deliver electrical current only to the first electrodes. In a second energized state, the electrical connections deliver electrical current to all of the electrodes.

21 Claims, 15 Drawing Sheets

U.S. PATENT DOCUMENTS

| | | | | |
|---|---|---|---|---|
| 5,658,281 | A * | 8/1997 | Heard | 606/48 |
| 5,700,261 | A | 12/1997 | Brinkerhoff | |
| 5,766,166 | A | 6/1998 | Hooven | |
| 5,776,128 | A | 7/1998 | Eggers | |
| 5,827,281 | A | 10/1998 | Levin | |
| 5,860,975 | A | 1/1999 | Goble et al. | |
| 5,891,140 | A | 4/1999 | Ginn et al. | |
| 5,893,846 | A * | 4/1999 | Bales et al. | 606/32 |
| 5,921,984 | A | 7/1999 | Sutcu et al. | |
| 5,951,549 | A | 9/1999 | Richardson et al. | |
| 5,954,720 | A | 9/1999 | Wilson et al. | |
| 5,976,132 | A | 11/1999 | Morris | |
| 6,030,381 | A | 2/2000 | Jones et al. | |
| 6,030,384 | A | 2/2000 | Nezhat | |
| 6,059,778 | A | 5/2000 | Sherman | |
| 6,086,586 | A | 7/2000 | Hooven | |
| 6,090,108 | A | 7/2000 | McBrayer et al. | |
| 6,126,658 | A | 10/2000 | Baker | |
| 6,179,837 | B1 | 1/2001 | Hooven | |
| 6,193,718 | B1 | 2/2001 | Kortenbach et al. | |
| 6,312,430 | B1 | 11/2001 | Wilson et al. | |
| 6,350,264 | B1 | 2/2002 | Hooven | |
| 6,391,029 | B1 | 5/2002 | Hooven et al. | |
| 6,447,511 | B1 | 9/2002 | Slater | |
| 6,464,701 | B1 | 10/2002 | Hooven et al. | |
| 6,558,384 | B2 | 5/2003 | Mayenberger | |
| 6,562,035 | B1 | 5/2003 | Levin | |
| 6,736,813 | B2 | 5/2004 | Yamauchi et al. | |
| 6,740,080 | B2 | 5/2004 | Jain et al. | |
| 6,749,609 | B1 | 6/2004 | Lunsford et al. | |
| 7,052,496 | B2 | 5/2006 | Yamauchi | |
| 2002/0019632 | A1 * | 2/2002 | Mayenberger | 606/48 |
| 2002/0107517 | A1 | 8/2002 | Witt et al. | |
| 2003/0130656 | A1 | 7/2003 | Levin | |
| 2004/0068307 | A1 | 4/2004 | Goble | |
| 2004/0199160 | A1 | 10/2004 | Slater | |

OTHER PUBLICATIONS

European Patent Office, Supplementary European Search Report dated May 3, 2011 for European Patent Application No. EP 07 79 9396.

International Searching Authority/US, Commissioner for Patents, The International Search Report and the Written Opinion of the International Searching Authority for International Application No. PCT/US07/73045, mailed Jul. 3, 2008.

* cited by examiner

BIPOLAR ELECTROSURGICAL SCISSORS

CROSS-REFERENCE TO RELATED APPLICATIONS

This application is a continuation of U.S. patent application Ser. No. 11/460,292, filed on Jul. 27, 2006, issued on Sep. 2, 2008 and is now U.S. Pat. No. 7,419,490, the entire disclosure of which is hereby incorporated by reference as if set forth in full herein.

BACKGROUND OF THE INVENTION

This invention relates generally to the field of minimally invasive surgery, and in particular to a hand-held, bipolar laparoscopic device for electrical or mechanical cutting of biological tissue and for coagulation of the tissue.

Nearly every open and laparoscopic surgical procedure requires the cutting and sealing of vascularized tissue. To reduce or minimize bleeding of the tissue, conventional surgical scissors have begun to be replaced with electrically energized scissors in monopolar and bipolar configurations, each offering certain advantages and disadvantages. Monopolar refers to a configuration where a return electrode is coupled to a patient, typically in the form of a patch coupled to the patient's skin, so that only one active electrode need be carried on the surgical instrument. With the monopolar technique, a concentrated electrical current is delivered from the active electrode on the instrument to targeted tissue, causing coagulation that stops bleeding. The electricity then disperses and flows through the patient en route to the return electrode attached to the patient's skin. Bipolar refers to a configuration wherein the instrument carries both the active and return electrodes, delivering energy to tissue between the two electrodes.

Monopolar electrosurgical instruments facilitate several surgical functions, such as cutting tissue, coagulating tissue to stop bleeding, or concurrently cutting and coagulating tissue. The surgeon can apply a current whenever the conductive portion of the instrument is in electrical contact with the patient, permitting the surgeon to operate with monopolar instruments from many different angles. However, as stated above, monopolar electrosurgical instruments do have some drawbacks, especially when used for laparoscopic procedures.

During laparoscopic monopolar electrosurgery, the view of the surgical field is somewhat constricted. The surgeon operates from the exterior of the patient's body using remote instrumentation. The manipulation of instruments and tissue is based on magnified images that are relayed from a camera connected to a laparoscope and displayed on a monitor. The active electrode may be in close proximity to other conductive instruments and to tissue, and may result in stray electrical current being transmitted to unseen tissue off the extended shaft of the remote laparoscopic instruments, possibly leading to thermal injury to the patient.

Stray currents may cause patient injury outside the laparoscope's view via direct coupling, insulation failure, or capacitive coupling. Direct coupling occurs when the active electrode touches another metal instrument within the patient, such as in the abdomen, transferring energy to the second instrument and possibly injuring tissue with which it comes in contact.

Insulation failure occurs when the insulated shaft of the electrode, which is designed to protect against the release of stray electrical current, becomes compromised due to insulation breakdown. The breakdown along the unseen shaft of an activated electrode can allow electrical current to leak into surrounding non-targeted tissue, causing unobserved damage.

Capacitive coupling occurs when electrical current is induced from the active electrode to nearby conductive material, despite intact insulation. During electrosurgery, the charge on the active electrode switches from highly positive to highly negative at a very high frequency. The rapidly varying electrical field around the active electrode is only partially impeded by electrical insulation and creates stray electrical currents by alternately attracting and repelling ions in surrounding body tissue. The movement of electrically charged ions in capacitively coupled tissue can cause currents that can heat tissue sufficiently to produce a burn.

In comparison to monopolar surgical instruments, such as monopolar scissors, the electrical current in a bipolar arrangement is not required to travel long distances through the patient before returning to the return electrode, thereby greatly reducing the minute risk of accidental burns. Instead, a bipolar electrode arrangement applies electrical current only between two energized cutting blades which are closely spaced and always within the field of view of the surgeon. A bipolar arrangement also requires less electrical power than a monopolar arrangement because the electrical current disperses through a much smaller volume of tissue. More importantly, a bipolar arrangement eliminates the possibility of accidental burns through an insulation failure of the active shaft and greatly reduces the risk of direct coupling and capacitive coupling. However, bipolar instruments require the surgeon to carefully position the instrument to ensure that both the active and return electrodes are in electrical contact with the patient before applying a current. This may limit the range of motion and the angle from which the surgeon can effectively use the bipolar instrument.

There are several variations for placement of electrodes on electrosurgical scissors that allow electrical current to flow through the cut tissue. For example, the exterior surface of one shearing member can include an active electrode while the exterior surface of the other shearing member can include a return electrode. In this configuration, electrosurgical current can flow from the exterior surface of one blade, through the cut tissue, to the exterior surface of the other blade.

In another variation, each of the two shearing surfaces includes an active electrode, while each of the two exterior surfaces includes a return electrode, or vice versa. In this configuration, electrical current can flow from each shearing surface, through the cut tissue, to an exterior surface, or vice versa.

Apart from mechanical cutting, the practicality of monopolar scissors makes them more favorable to surgeons. Monopolar scissors not only permit a surgeon to coagulate tissue between the blades prior to cutting the tissue mechanically, but they also permit the surgeon to dissect thin connective tissue electrically by moving one blade in a sweep-like motion over the tissue. Monopolar scissors also permit electrosurgical coagulation of small blood vessels that are cut open during a mechanical cutting process. This is typically performed by energizing the tissue with the exterior surface of one of the scissor blades.

Conventional bipolar scissors also permit electrical coagulation and cutting of the tissue between the blades, but they do not allow for the common practice to utilize one blade for dissection of tissue by moving the blade in a sweep-like motion over the tissue. Conventional bipolar scissors also do not allow for simultaneous coagulation of tissue between the blades and surrounding tissue, or coagulating the tissue by energizing it with the exterior surface of one of the blades.

This is due to the common approach to separate the high frequency (HF) coagulation and mechanical cutting action both spatially and functionally by arranging the active, electrically conductive, radio frequency (RF) electrodes on the outside of each electrically conductive blade, while being electrically insulated through insulators, such as ceramic or plastic.

One improved bipolar scissors includes blades having electrodes on the inner surface of each blade with the electrodes being connected to the same pole to avoid a short circuit between the mating inner faces of the blades. The outer surface of each of the blades includes at least two electrodes connected to opposite poles, meaning that at least one of the electrodes on the outer surface of each blade is connected to the same pole as the electrode on the inner surface of the blade. With these scissors, all of the electrodes are energized simultaneously and there are no means to have less than all of the electrodes energized when applying electrical current to the electrodes. In this manner, it is not possible to coagulate only the tissue between the blades. If an electrical current is applied while cutting the tissue, the surrounding tissue is also coagulated.

SUMMARY OF THE INVENTION

The deficiencies of the prior art are overcome with the present invention, which includes a bipolar electrosurgical scissors for use in treating biological tissue. The bipolar electrosurgical scissors includes a first and second scissor blade. Each of the first and second scissor blades has a shearing surface, an opposed surface that is opposite the shearing surface, a cutting edge, a first, proximal end, and a second, distal end. The shearing surface and cutting edge of each of the scissor blades is electrically neutral. The shearing surface of the first blade and the shearing surface of the second blade face each other and interface with each other. A pivot pin pivotally couples the first scissor blade to the second scissor blade at a position that is proximal to the shearing surfaces of the first and second scissor blades. The bipolar electrosurgical scissors also include a first electrical connection for receiving an electrical current of a first polarity and a second electrical connection for receiving an electrical current of a second polarity, which is opposite to the first polarity. Each of the first and second scissor blades includes at least one exposed first electrode and at least one exposed second electrode positioned on the opposed surface of the respective scissor blade and extending lengthwise along the length of the respective scissor blade. The at least one first electrode on the first scissor blade is coupled to the first electrical connection. The at least one second electrode on the first scissor blade is coupled to the second electrical connection. The at least one first electrode on the second scissor blade is coupled to the second electrical connection. The at least one second electrode on the second scissor blade is coupled to the first electrical connection. In a first energized state, the first electrical connection delivers electrical current only to the at least one first electrode on the first scissor blade and the second electrical connection delivers electrical current only to the at least one first electrode on the second scissor blade. In a second energized state, the first electrical connection delivers electrical current to the at least one first electrode on the first scissor blade and to the at least one second electrode on the second scissor blade. In the second energized state, the second electrical connection delivers electrical current to the at least one second electrode on the first scissor blade and to the at least one first electrode on the second scissor blade.

In another aspect, the distance between the at least one first electrode and the at least one second electrode on the opposed surface of each of the first and second scissor blades is sufficient to prevent electrical arcing between the electrodes, and small enough to permit simultaneous connection between the tissue and two respective electrodes having opposing polarity.

In another aspect, each of the first and second scissor blades includes a laminated structure having a first layer, a second layer, a third layer, a fourth layer and a fifth layer. The first layer on each of the first and second scissor blades coincides with the shearing surface and cutting edge of the respective scissor blade and includes a first, shearing surface and a second, opposed surface. The first surface of the first layer forms the shearing surface of the respective blade. The second layer is coupled to the second surface of the first layer. The second layer is electrically nonconductive and includes a material that insulates against electrical current. The third layer is coupled to the second layer on the side opposite the first layer. The third layer is electrically conductive and exposed portions of the third layer form the at least one first electrode of the respective scissor blade. The fourth layer is coupled to the third layer on the side opposite the second layer. The fourth layer is electrically nonconductive and includes a material that insulates against electrical current. The fifth layer is coupled to the fourth layer on the side opposite the third layer. The fifth layer is electrically conductive and exposed portions of the fifth layer form the at least one second electrode of the respective scissor blade. In another facet, the second layer of each of the first and second scissor blades completely separates the third layer from the first layer and provides insulation between the third layer and the first layer of the respective scissor blade. Likewise, the fourth layer of each of the first and second scissor blades completely separates the third layer from the fifth layer and provides insulation between the third layer and the fifth layer of the respective scissor blade. In another facet, the electrically insulating material of the second and fourth layers of the first and second scissor blades has sufficient dielectric strength to substantially prevent electrical breakdown of the electrically insulating material. In another facet, the exposed surfaces of the third layer of each of the first and second scissor blades forms at least two first electrodes and the exposed surfaces of the fifth layer of each of the first and second scissor blades form at least one second electrode. In another facet, the exposed surfaces of the fifth layer of each of the first and second scissor blades forms one second electrode positioned between the at least two first electrodes of the respective scissor blade.

In another aspect, the first layer of each of the first and second scissor blades includes a first edge surface, which coincides with the cutting edge, and a second edge surface. In another facet, the scissors include an electrically insulating coating on the first layer of each of the first and second scissor blades. The electrically insulating coating covers the shearing surface, the cutting edge, the portion of the first edge surface proximate the shearing surface and the portion of the second edge surface proximate the shearing surface. The first layer of each of the blades includes at least one first electrode positioned on each of the first and second edge surfaces at the portions of the first and second edge surfaces that are proximate the opposed surface of the respective first layer. The portions of the first and second edge surfaces of the first layers on the first and second scissor blades that form the first electrodes on the first layers are not covered with the electrically insulating coating. In another facet, the electrically insulating coating on the shearing surfaces of the first and second scissor blades includes an amorphous diamond-like carbon. In another facet, the exposed surfaces of the third layers of each of the first and second scissor blades form at least two second electrodes of the respective blade. The exposed surfaces of the fifth layer of each of the first and second scissor blades form at least one first electrode of the respective blade. In another facet, in the first energized state, the first electrical connection delivers electrical current only to the first electrodes positioned on the first layer of the first scissor blade and the second electrical connection delivers electrical current only to the first electrodes positioned on the first layer of the second scissor blade. In another facet, the distance between the first electrodes on the first and second edge surfaces of adjacent first layers of the first and second scissor blades, with the scissors in a closed condition, is sufficient to prevent electrical arcing between the electrodes. The distance between the first electrodes on the first and second edge surfaces of adjacent first layers of the first and second scissor blades, with the scissors in a closed condition, is small enough to permit simultaneous connection between the tissue and a first electrode on the first scissor blade and a first electrode on the second scissor blade.

In another aspect, each of the first and second scissor blades of the bipolar electrosurgical scissors includes an insulating body having a primary surface that corresponds with the shearing surface of the blade and a secondary surface that corresponds with the opposed surface of the blade. Each of the first and second scissor blades also includes a shearing layer that has a first, shearing surface, a second, opposed surface, and the cutting edge. The opposed surface of the shearing layer is coupled to the primary surface of the insulating body. The at least one first electrode and the at least one second electrode are coupled to, inlayed into, or deposited onto the secondary surface of the insulating body of each of the first and second scissor blades. The first and second electrodes are positioned in an alternating relationship with the first and second electrodes on the second scissor blade corresponding with the first and second electrodes on the first scissor blade. In another facet, the distance between the at least one first electrode and the at least one second electrode on the opposed surface of each of the first and second scissor blades is sufficient to prevent electrical arcing between the electrodes in an open configuration, and small enough to permit simultaneous connection between the tissue and two respective electrodes having opposing polarity. In another facet, the material that forms the electrically insulating body of each of the first and second scissor blades has sufficient dielectric strength to substantially prevent electrical breakdown of the electrically insulating body.

In another aspect, the shearing layer of each of the first and second scissor blades includes a first edge surface and a second edge surface. The first edge surface coincides with the cutting edge of the respective blades. In another facet, the scissors include an electrically insulating coating on the shearing layer of the first and second scissor blades. The electrically insulating coating covers the shearing surface, the cutting edge, the portion of the first edge surface proximate the shearing surface and the portion of the second edge surface proximate the shearing surface. The scissors also include at least one first electrode positioned on each of the first and second edge surfaces of the shearing layer of each of the first and second scissor blades at the portion of the respective edge surface that is proximate the opposed surface of the respective shearing layer. In another facet, the electrically insulating coating on the shearing surfaces of the first and second scissor blades includes an amorphous diamond-like carbon. In another facet, in the first energized state, the first electrical connection delivers electrical current only to the first electrodes positioned on the shearing layer of the first scissor blade and the second electrical connection delivers electrical current only to the first electrodes positioned on the shearing layer of the second scissor blade. In another facet, the distance between the first electrodes on the first and second edge surfaces of adjacent shearing layers of the first and second scissor blades, with the scissors in a closed condition, is sufficient to prevent electrical arcing between the electrodes. The distance between the first electrodes on the first and second edge surfaces of adjacent shearing layers of the first and second scissor blades, with the scissors in a closed condition, is small enough to permit simultaneous connection between the tissue and a first electrode on the first scissor blade and a first electrode on the second scissor blade.

These and other features and advantages of the invention will be clarified with a description of the embodiments and reference to the associated drawings.

DESCRIPTION OF THE INVENTION

The invention and its various embodiments can now be better understood with the following detailed description wherein illustrated embodiments are described. It is to be expressly understood that the illustrated embodiments are set forth as examples and not by way of limitations on the invention.

Figure 1:
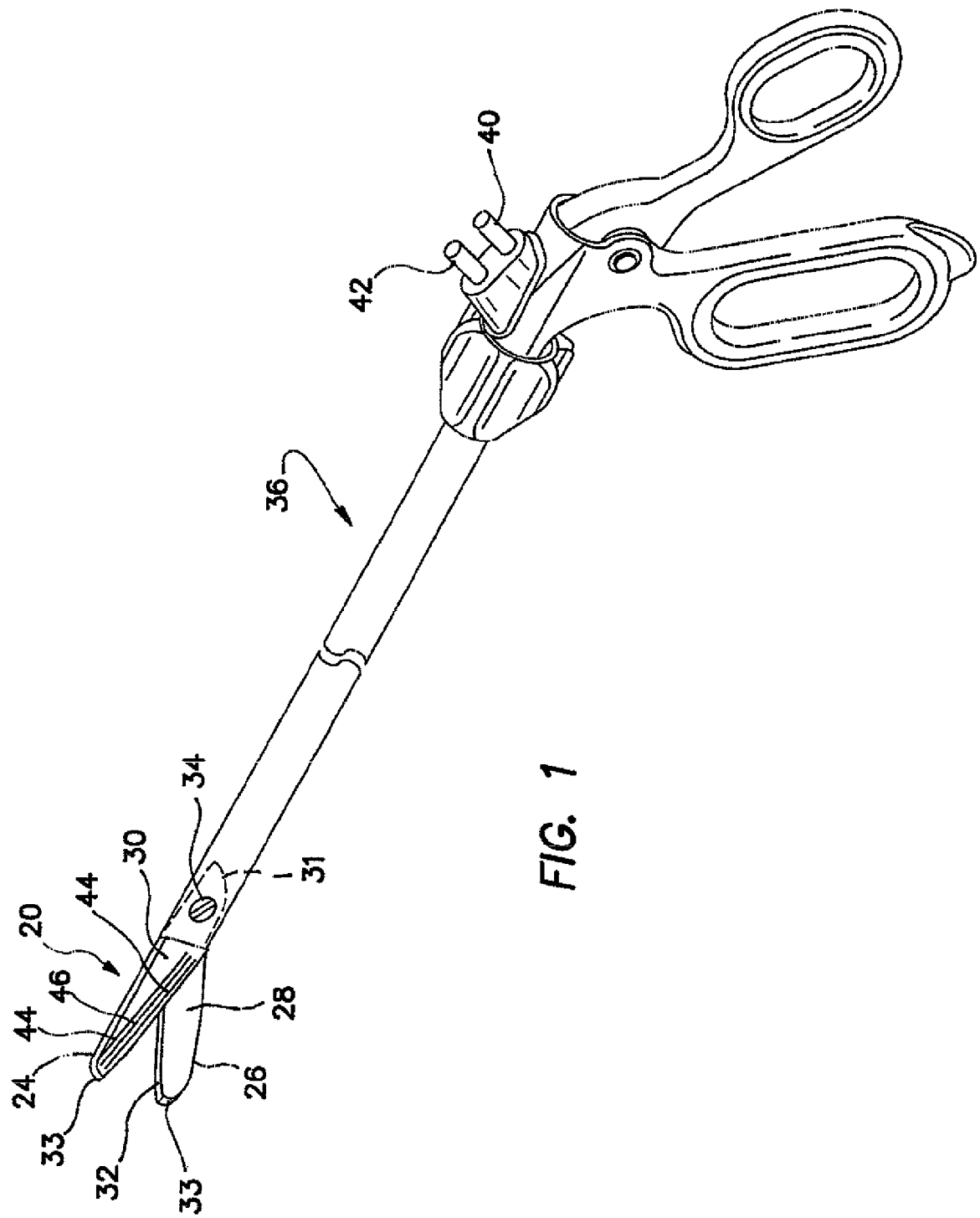
FIG. 1 is a perspective view depicting a bipolar electrosurgical scissors of the present invention incorporated into laparoscopic scissors.
Figure 2:
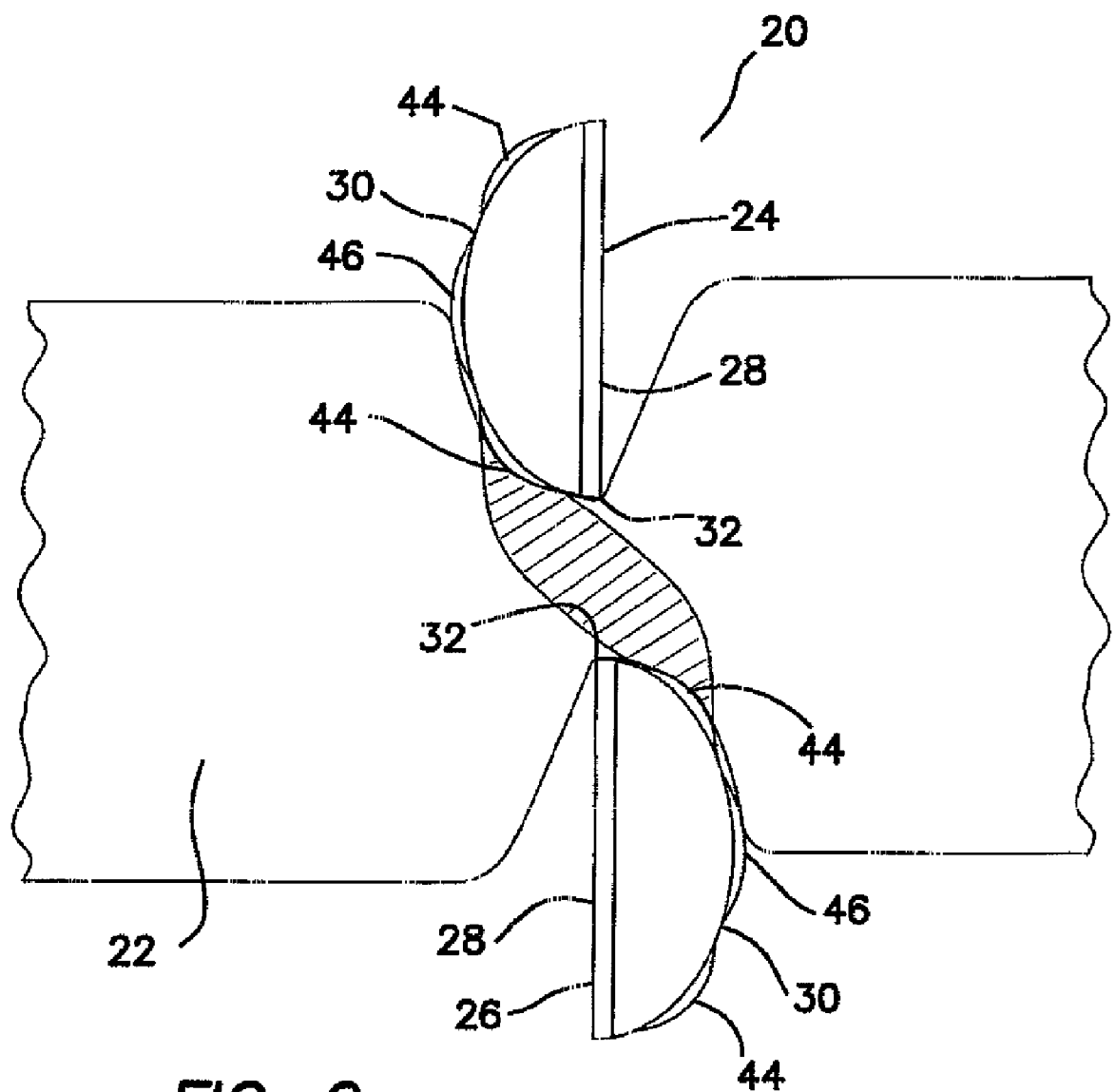
FIG. 2 is an end view of the blades of the bipolar electrosurgical scissors of FIG. 1 depicting the blades in an open condition with biological tissue positioned between the blades and the scissors energized in a first energized state with just the tissue between the blades being energized.
Figure 3:
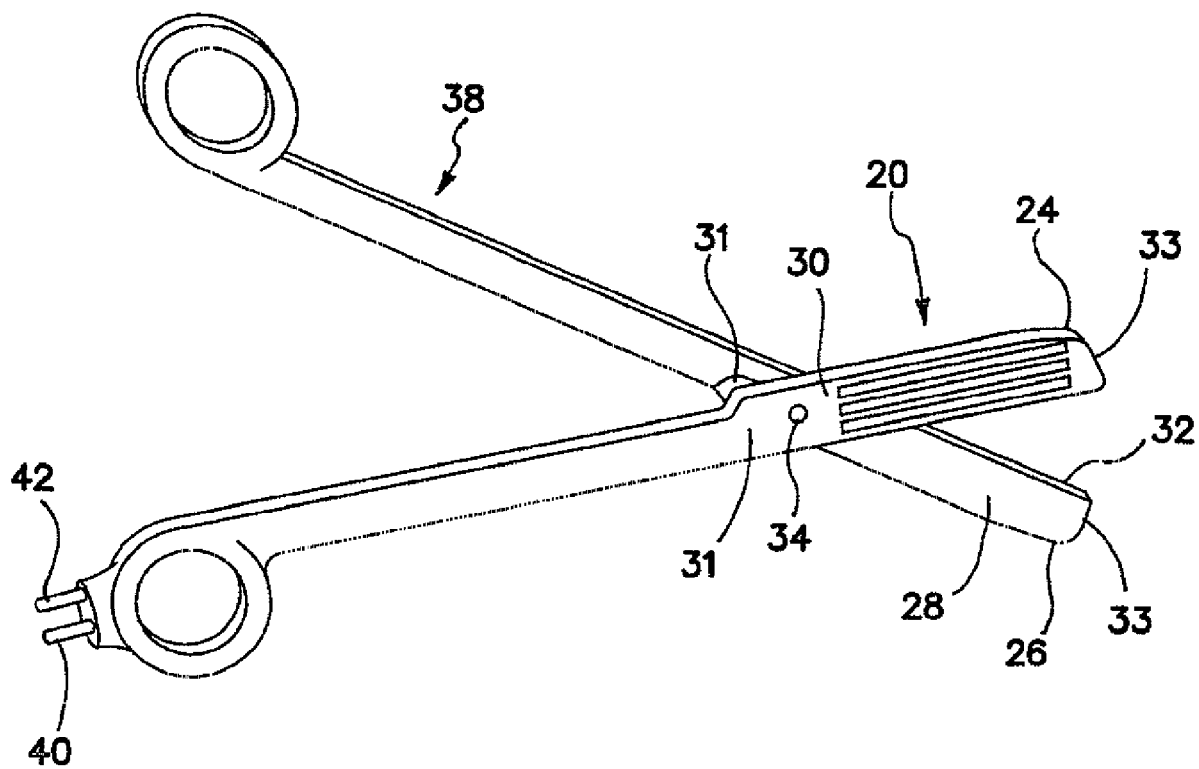
FIG. 3 is a perspective view of the bipolar electrosurgical scissors of the present invention incorporated into conventional surgical scissors.

Referring to FIGS. 1-2, the invention includes bipolar electrosurgical scissors 20 for use in treating biological tissue 22. The scissors 20 include a first scissor blade 24 and a second scissor blade 26. Each of the first and second blades 24, 26 includes a shearing surface 28, an opposed surface 30 positioned opposite the shearing surface, a cutting edge 32, a first, proximal end 31, and a second, distal end 33. A pivot pin 34 pivotally couples the first blade 24 to the second blade 26 at a position proximal the shearing surfaces 28 of the first and second blades. The shearing surfaces 28 of the first and second blades 24, 26 face each other and interface with each other. As depicted in FIG. 1, the scissors 20 may be part of a laparoscopic surgical instrument 36. Alternatively, as depicted in FIG. 3, the scissors 20 may be part of conventional electrosurgical shears 38 to be used in conventional, open surgery.

With continuing reference to FIG. 1, the scissors 20 include first and second electrical connections 40, 42. The first electrical connection 40 receives an electrical current of a first polarity, and the second electrical connection 42 receives an electrical current of a second polarity that is opposite to the electrical current of the first polarity.

Referring to FIG. 2, each of the first and second scissor blades 24, 26 includes at least one first electrode 44 and at least one second electrode 46. Each of the first and second electrodes 44, 46 is positioned on the opposed surface 30 of the respective blade. The at least one first electrode 44 on the first blade is coupled to the first electrical connection 40 (FIG. 1). The at least one second electrode 46 on the first blade 26 is coupled to the second electrical connection 42 (FIG. 1). The at least one first electrode 44 on the second blade 26 is coupled to the second electrical connection 42. The at least one second electrode 46 on the second blade 26 is coupled to the first electrical connection 40. Each of the first and second electrodes 44, 46 includes a portion that is exposed on the opposed surface 30 of the respective blade 24, 26. The first and second electrodes 44, 46 extend lengthwise along the length of the opposed surfaces 30 of the first and second blades 24, 26. The shearing surface 28 of each of the blades 24, 26 is not coupled to either of the first and second electrical connections 40, 42. Moreover, the shearing surface 28 of each of the first and second blades 24, 26 is electrically neutral. As will be described in more detail below, the shearing layer of each of the blades may be coupled to opposing first and second electrodes 44, 46, and first and second edge surfaces of the shearing layers of each of the blades 24, 26 may include a first electrode. As will also be described in more detail below, the first and second electrodes 44, 46 are all separated by an insulating material.

With continuing reference to FIG. 2, in a first energized state, the first electrical connection 40 delivers electrical current only to the at least one first electrode 44 on the first scissor blade 24 and the second electrical connection 42 delivers electrical current only to the at least one first electrode 44 on the second scissor blade 26. In a second energized state (see FIG. 4), the first electrical connection 40 (FIG. 1) delivers electrical current to the at least one first electrode 44 on the first blade 24 and to the at least one second electrode 46 on the second blade 26 while the second electrical connection 42 (FIG. 1) delivers electrical current to the at least one second electrode 46 on the first blade 24 and to the at least one first electrode 44 on the second blade 26.

Figure 5:
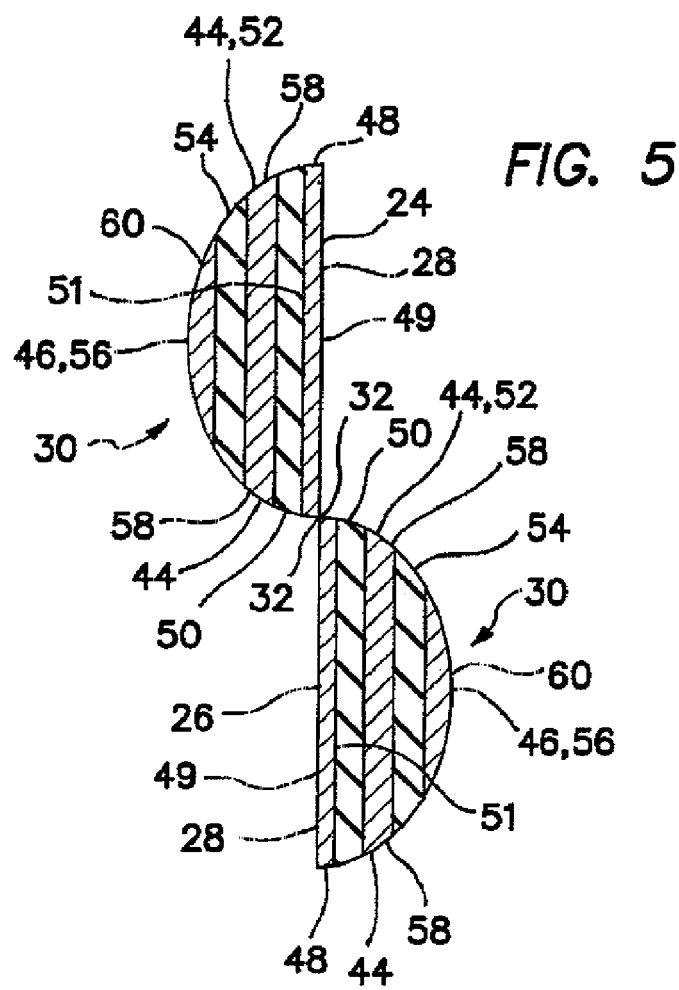
FIG. 5 is an end view, in cross-section, depicting the blades of the bipolar electrosurgical scissors with the blades in a laminated configuration.

Referring to FIG. 5, the first and/or second scissor blade 24, 26 may include a laminated structure. FIG. 5 depicts each of the first and second blades 24, 26 including the laminated structure including at least a first, shearing layer 48, a second layer 50, a third layer 52, a fourth layer 54 and a fifth layer 56.

The first layer 48 coincides with the shearing surface 28 and cutting edge 32 of the scissor blades 24, 26. The first layer 48 includes a first, shearing surface 49 and a second, opposed surface 51, and is made of a material capable of forming a desirable cutting edge, such as a metal or other materials that are well known in the art. As stated above, the shearing surface 28 of each of the first and second blades 24, 26 is electrically neutral. Thus, the first layer 48 is not coupled to either of the first or second electrical connections 40, 42. The second layer 50 is coupled to the second surface 51 of the first layer 48. The third layer 52 is coupled to the second layer 50 on the side opposite the first layer 48. The third layer 52 is electrically conductive. The fourth layer 54 is coupled to the third layer 52 on the side opposite the second layer 50. The fifth layer 56 is coupled to the fourth layer 54 on the side opposite the third layer 52. The fifth layer 56 is electrically conductive.

With continuing reference to FIG. 5, the third layer 52 of each of the scissor blades 24, 26 includes exposed portions 58 that form the at least one first electrode 44 of the first and second blades. The third layer 52 on the first blade 24 is coupled to the first electrical connection 40 (FIG. 1) and the third layer 52 on the second blade 26 is coupled to the second electrical connection 42 (FIG. 1). The second layer 50 completely separates the third, conductive layer 52 from the first, neutral layer 48. The second layer 50 is electrically nonconductive and is formed of a material that insulates against electrical current to prevent the current delivered to the third layer from flowing to the first layer.

The fifth layer 56 includes exposed portions 60 that form the at least one second electrode 46 on each of the first and second scissor blades 24, 26. The fifth layer 56 on the first blade 24 is coupled to the second electrical connection 42 and the fifth layer 56 on the second blade 26 is coupled to the first electrical connection 40. The fourth layer 54 completely separates the fifth, conductive layer 56 from the third, conductive layer 52, and the third layer has opposing polarity to the fifth layer. The fourth layer 54 is electrically nonconductive and is formed of a material that insulates against electrical current to prevent shorting between the third and fifth 52, 56 layers on the respective blades 24, 26.

With further reference to FIG. 5, the electrically insulating material of the second and fourth layers 50, 54 of the first and second scissor blades 24, 26 has sufficient dielectric strength to substantially prevent electrical breakdown of the insulating material. The exposed surfaces 58 of the third layer 52 of the first and second blades 24, 26 may form at least two first electrodes 44 on each of the first and second blades. The exposed surfaces 60 of the fifth layer 56 of the first and second blades 24, 26 may form at least one second electrode 46 on each of the first and second blades. As depicted in FIG. 5, the exposed surfaces 60 of the fifth layer 56 of the first and second blades 24, 26 may form one second electrode 46 positioned between the at least two first electrodes 44 on each of the first and second blades. The shearing surfaces 28 and cutting edges 32 of the first and second blades 24, 26 may include a coating, such as a coating of amorphous diamond-like carbon or other suitable material that is well known in the art, to resist mechanical wear and friction between the blades.

Figure 6:
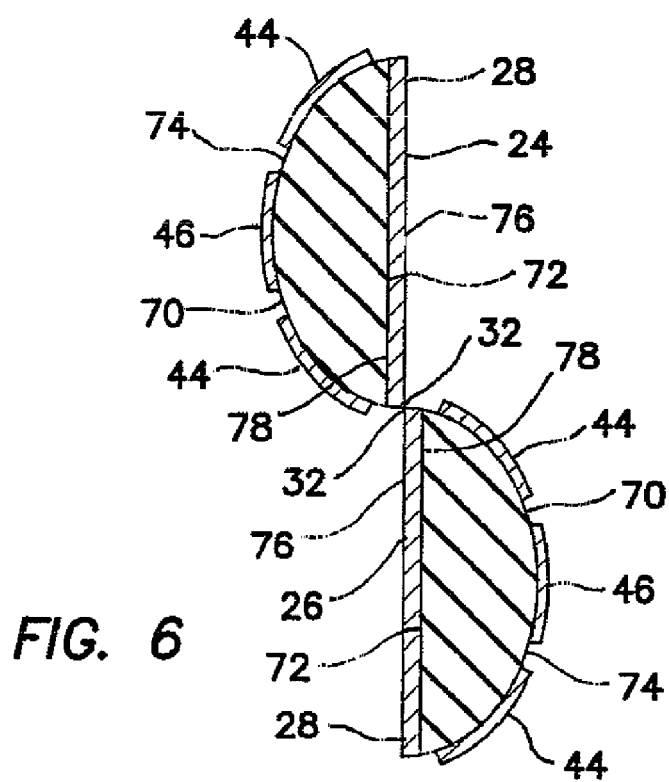
FIG. 6 is an end view, in cross-section, depicting the blades of the bipolar electrosurgical scissors with the electrodes being coupled onto an insulated body portion of the blades.

Referring to FIG. 6, the first and/or second scissor blade 24, 26 may include an insulating body with a shearing layer and electrodes coupled to the insulating body. In other embodiments, the first and second blades 24, 26 may include an insulating body with a shearing layer coupled to the insulating body and electrodes inlayed into the insulating body (FIG. 7), electrodes deposited onto the insulating body (FIG. 8), or include suitable electrodes in any other form that is well known in the art positioned on the insulating body. More particularly, each of the first and second blades 24, 26 includes an insulating body 70 having a primary surface 72 corresponding with the shearing surface 28, and a secondary surface 74 corresponding with the opposed surface 30. A shearing layer 76 is coupled to the primary surface 72 of the insulating body 70. The shearing layer 76 includes a first, shearing surface 28, a second, opposed surface 78, and the cutting edge 32. The second, opposed surface 78 of the shearing layer 76 is coupled to the primary surface 72 of the insulating body 70.

Figure 7:
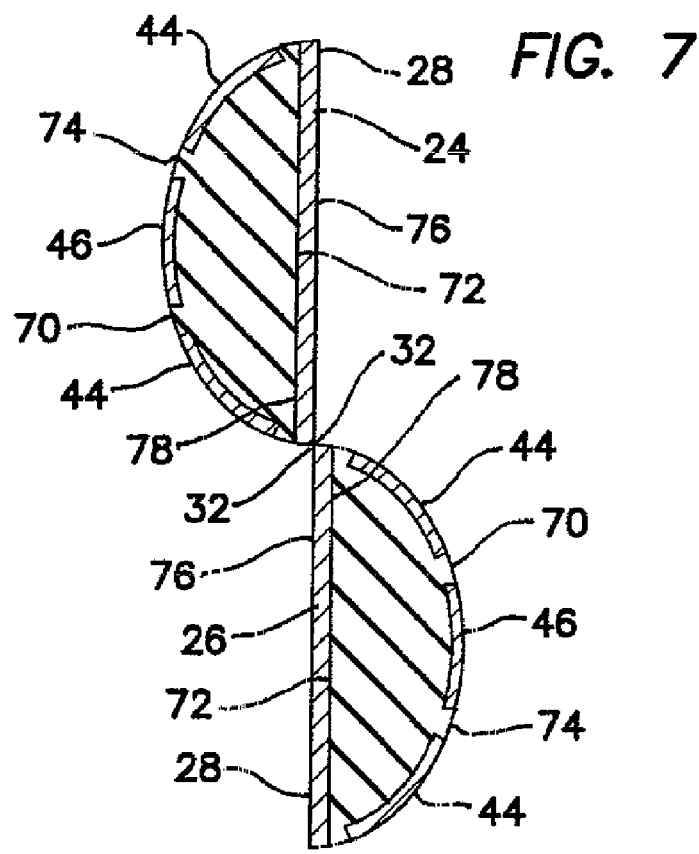
FIG. 7 is an end view, in cross-section, depicting the blades of the bipolar electrosurgical scissors with the electrodes being inlayed into an insulated body portion of the blades.
Figure 8:
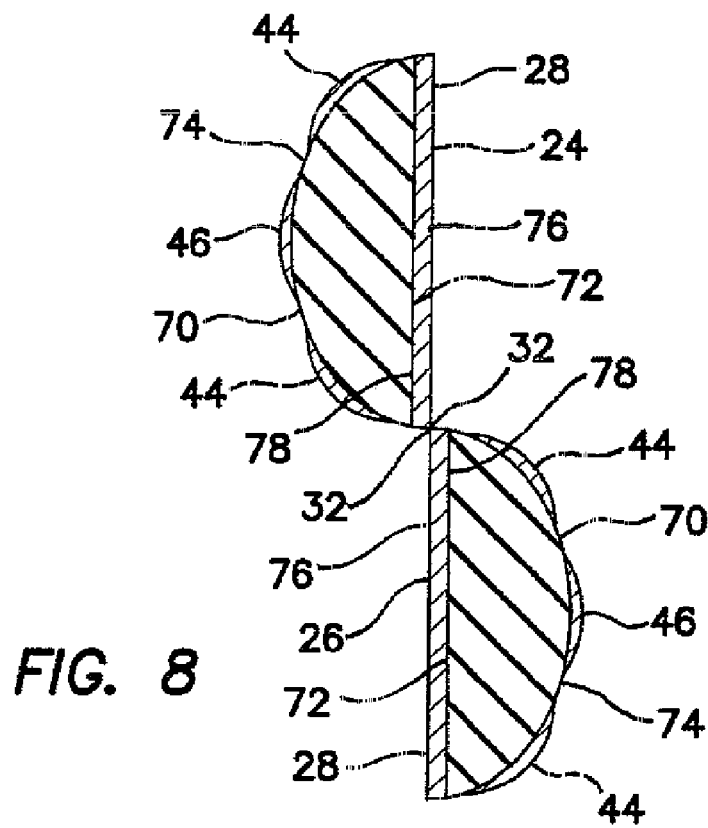
FIG. 8 is an end view, in cross-section, depicting the blades of the bipolar electrosurgical scissors with the electrodes being deposited onto an insulated body portion of the blades.

With continued reference to FIGS. 6-8, as the shearing layer 76 includes the shearing surface 28 and cutting edge 32 of the blades 24, 26, the shearing layer is made of a material capable of forming a desirable cutting edge, such as a metal or other material that is well known in the art. As stated above, the shearing surface 28 of each of the first and second blades 24, 26 is electrically neutral. Thus, the shearing layer 76 is not coupled to either of the first or second electrical connections 40, 42.

With further reference to FIGS. 6-8, the first scissor blade 24 may include the at least one first electrode 44 and the at least one second electrode 46 coupled to (FIG. 6), inlayed into (FIG. 7), or deposited onto (FIG. 8) the secondary surface 74 of the insulating body 70 of the first blade with the first and second electrodes positioned in an alternating relationship. The second scissor 26 blade may include the at least one first electrode 44 and the at least one second electrode 46 coupled to (FIG. 6), inlayed into (FIG. 7), or deposited onto (FIG. 8) the secondary surface 74 of the insulating body 70 of the second blade with the first and second electrodes positioned in an alternating relationship and corresponding to the first and second electrodes on the first blade. The electrically insulating material of which the insulating body 70 of the first and second scissor blades 24, 26 is formed has sufficient dielectric strength to substantially prevent electrical breakdown of the electrically insulating material.

Figure 9:
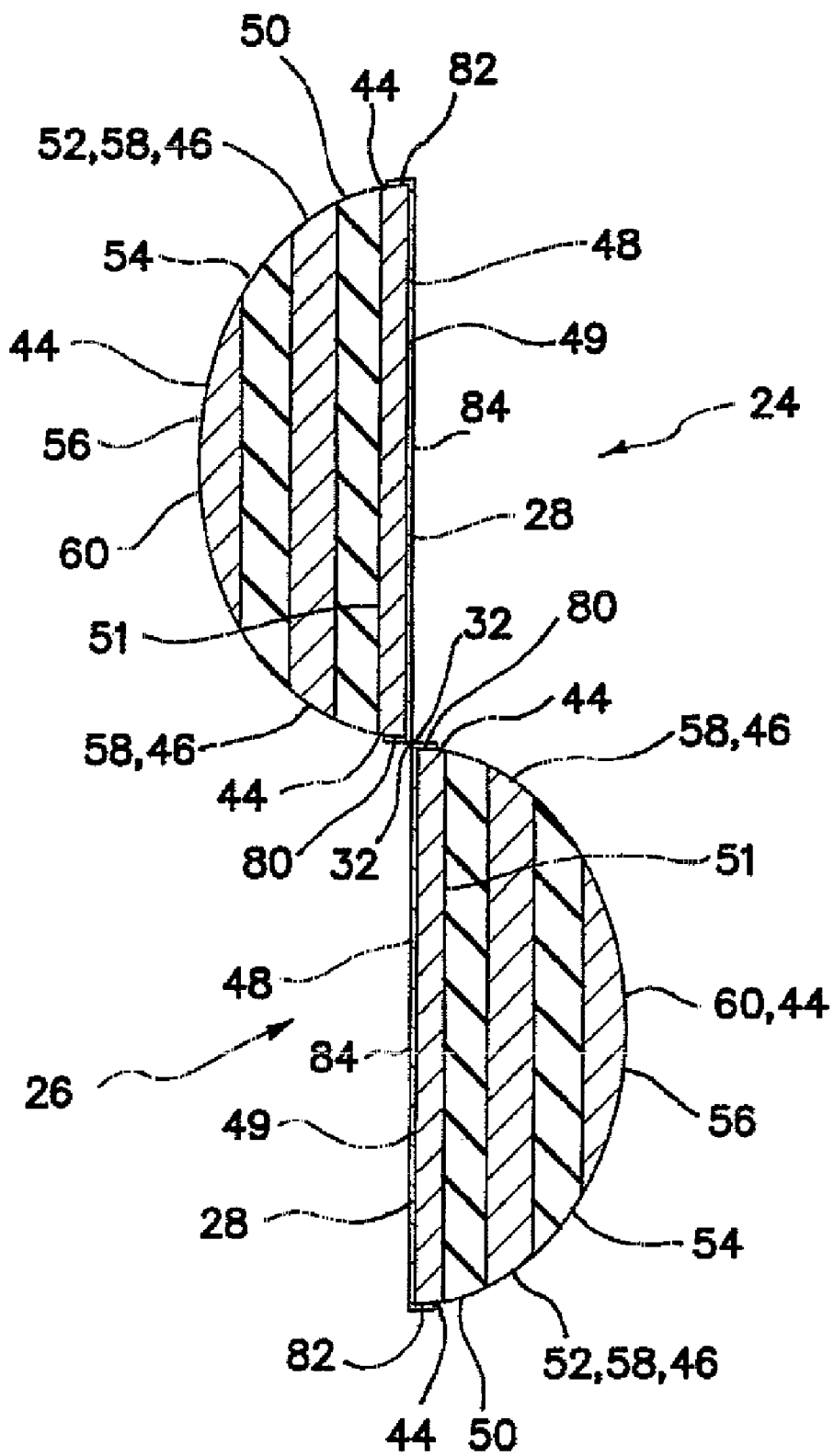
FIG. 9 is an end view, in cross-section, depicting the blades of the bipolar electrosurgical scissors with the blades in a laminated configuration, similar to FIG. 5 but having additional electrodes on the first layer of the blades.

Referring to FIG. 9, the first and/or second scissor blade 24, 26 may include a laminated structure similar to the laminated structure of FIG. 5 with each of the first and second scissor blades 24, 26 including at least the first layer 48, the second layer 50, the third layer 52, the fourth layer 54 and the fifth layer 56. FIG. 9 depicts each of the to first and second scissor blades 24, 26 including the laminated structure.

Similar to FIG. 5, the first layer 48 of FIG. 9 coincides with the shearing surface 28 and cutting edge 32 of the blades 24, 26. The first layer 48 includes the first, shearing surface 49 and second, opposed surface 51, and is made of a material capable of forming a desirable cutting edge, such as a metal or other materials that are well known in the art. The first layer 48 also includes a first and second edge surface 80, 82 with each edge surface including a first electrode 44. The first electrodes 44 on the first and second edge surfaces 80, 82 of the first blade 24 are coupled to the first electrical connection 40 (FIG. 1) and the first electrodes 44 on the first and second edge surfaces 80, 82 of the second blade 26 are coupled to the second electrical connection 42 (FIG. 1). The first edge surface 80 of the first layer 48 of each of the first and second blades 24, 26 coincides with the cutting edge 32 of the blades.

The second layer 50 of each of the first and second scissor blades 24, 26 is coupled to the second surface 51 of the first layer 48. The third layer 52 is coupled to the second layer 50 on the side opposite the first layer 48. The third layer 52 is electrically conductive. The fourth layer 54 is coupled to the third layer 52 on the side opposite the second layer 50. The fifth layer 56 is coupled to the fourth layer 54 on the side opposite the third layer 52. The fifth layer 56 is electrically conductive.

With continuing reference to FIG. 9, the third layer 52 of each of the scissor blades 24, 26 includes exposed portions 58 that form the at least one second electrode 46 of the first and second blades. The third layer 52 on the first blade 24 is coupled to the second electrical connection 42 (FIG. 1) and the third layer 52 on the second blade 26 is coupled to the first electrical connection 40 (FIG. 1). The second layer 50 completely separates the third, conductive layer 52 from the first, conductive layer 48.

The fifth layer 56 includes exposed portions 60 that form another first electrode 44 on each of the first and second scissor blades 24, 26. The fifth layer 56 on the first blade 24 is coupled to the first electrical connection 40 (FIG. 1) and the fifth layer 56 on the second blade 26 is coupled to the second electrical connection 42 (FIG. 1). The fourth layer 54 completely separates the fifth, conductive layer 56 from the third, conductive layer 52.

The third layer 52 has opposing polarity to the first and fifth layers 48, 56. The second and fourth layers 50, 54 are electrically nonconductive and are formed of materials that insulate against electrical current to prevent electrical shorting between the third layer 52 and the first and fifth layers 48, 56 on the respective blades.

With further reference to FIG. 9, the electrically insulating material of the second and fourth layers 50, 54 of the first and second scissor blades 24, 26 has sufficient dielectric strength to substantially prevent electrical breakdown of the insulating material. The exposed surfaces 58 of the third layer 52 of the first and second blades 24, 26 may form at least two second electrodes 46 on each of the first and second blades. The exposed surfaces 60 of the fifth layer 56 of the first and second scissor blades 24, 26 may form at least one first electrode 44 on each of the first and second scissor blades. As depicted in FIG. 9, the exposed surfaces 60 of the fifth layer 56 of the first and second scissor blades 24, 26 may form one first electrode 44 positioned between the at least two second electrodes 46 on each of the first and second blades.

With the first layer 48 of the first scissor blade 24 being coupled to the first electrical connection 40 and the first layer 48 of the second scissor blade 26 being coupled to the second electrical connection 42, it is necessary to electrically insulate the mating and interfacing portions of the first layer of each of the blades to prevent electrical shorting between the blades. Referring to FIG. 9, the shearing surfaces 28 and cutting edges 32 of each of the first and second blades 24, 26 may include an electrically insulating coating 84, such as a coating of amorphous diamond-like carbon or other suitable electrically insulating material that is well known in the art. An amorphous diamond-like coating facilitates the prevention of electrical shorting through metallic blades 24, 26 and resists mechanical wear and friction between the blades. On each of the first and second scissor blades 24, 26, portions of the first edge surface 80 and the second edge surface 82 proximate the shearing surface 28 are also coated with the electrically insulating coating 84 to facilitate the prevention of electrical shorting through the blades. The portions of the first edge surface 80 and the second edge surface 82 that are proximate the second, opposed surface 51 of each of the first and second scissor blades 24, 26 are not covered with the electrically insulating coating 84 and, thereby, function as first electrodes 44 for each of the scissor blades.

Figure 10:
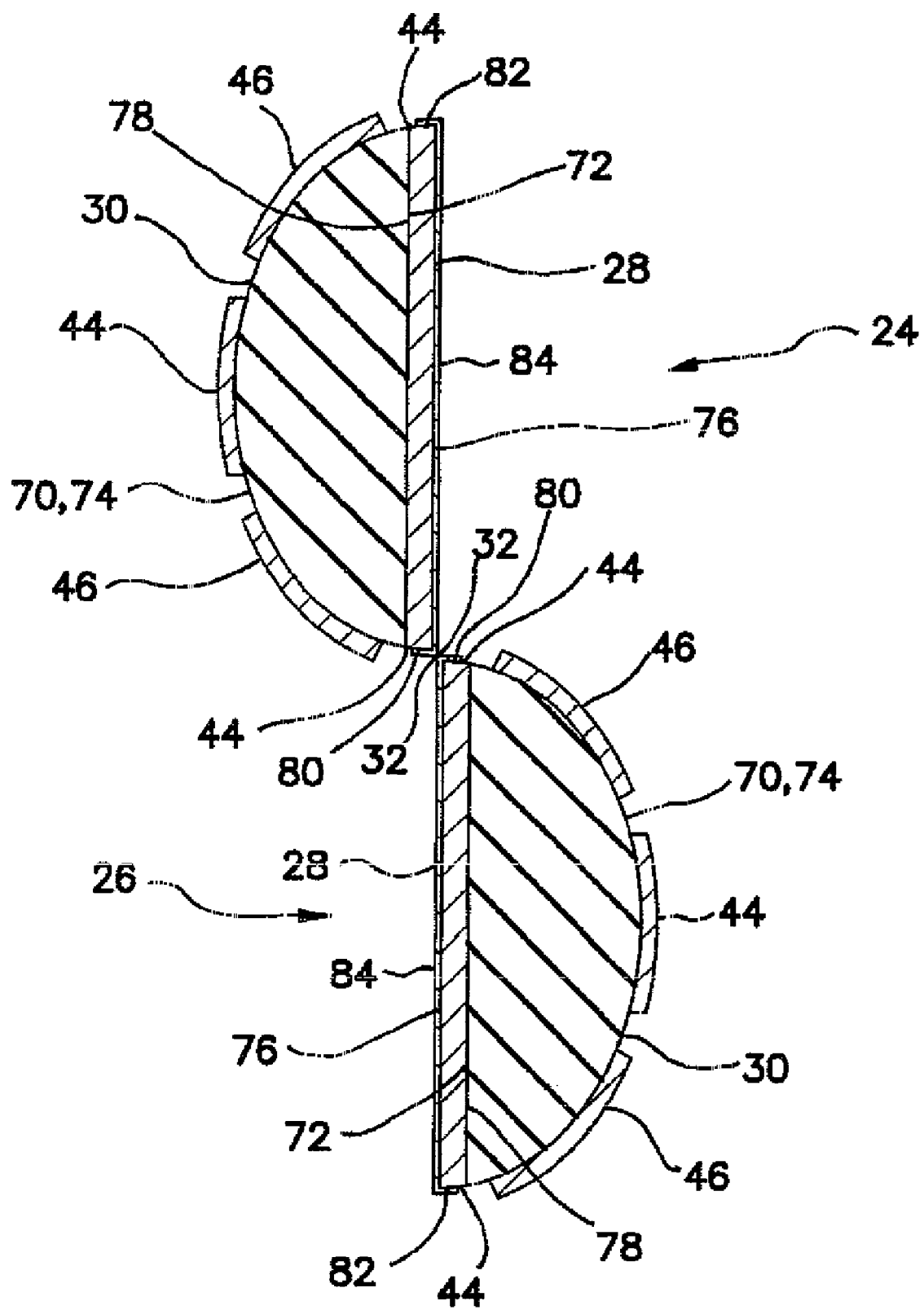
FIG. 10 is an end view, in cross-section, depicting the blades of the bipolar electrosurgical scissors with the electrodes being coupled onto an insulated body portion of the blades, similar to FIG. 6 but having additional electrodes on the shearing layer of the blades.
Figure 11:
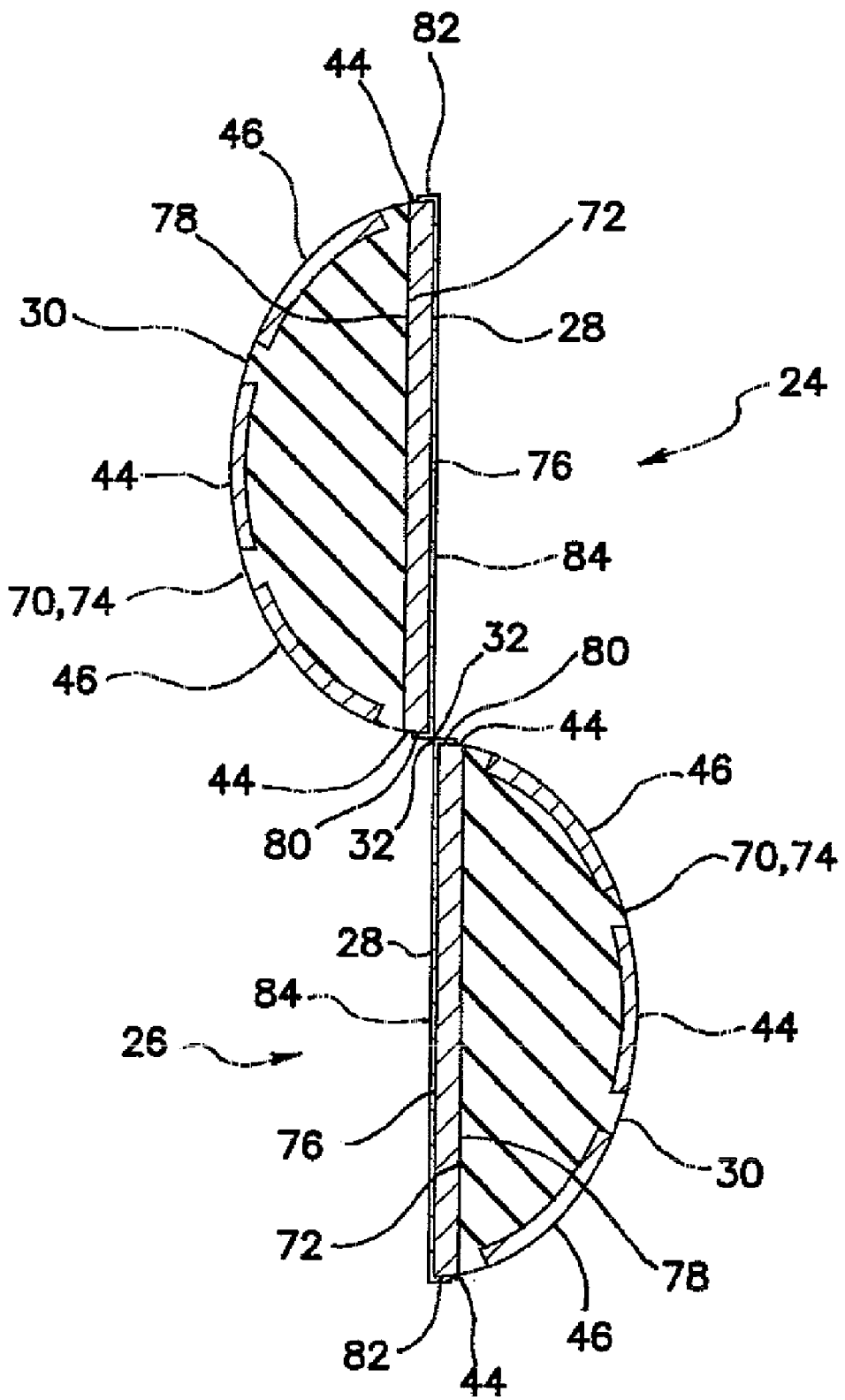
FIG. 11 is an end view, in cross-section, depicting the blades of the bipolar electrosurgical scissors with the electrodes being inlayed into an insulated body portion of the blades, similar to FIG. 7 but having additional electrodes on the shearing layer of the blades.
Figure 12:
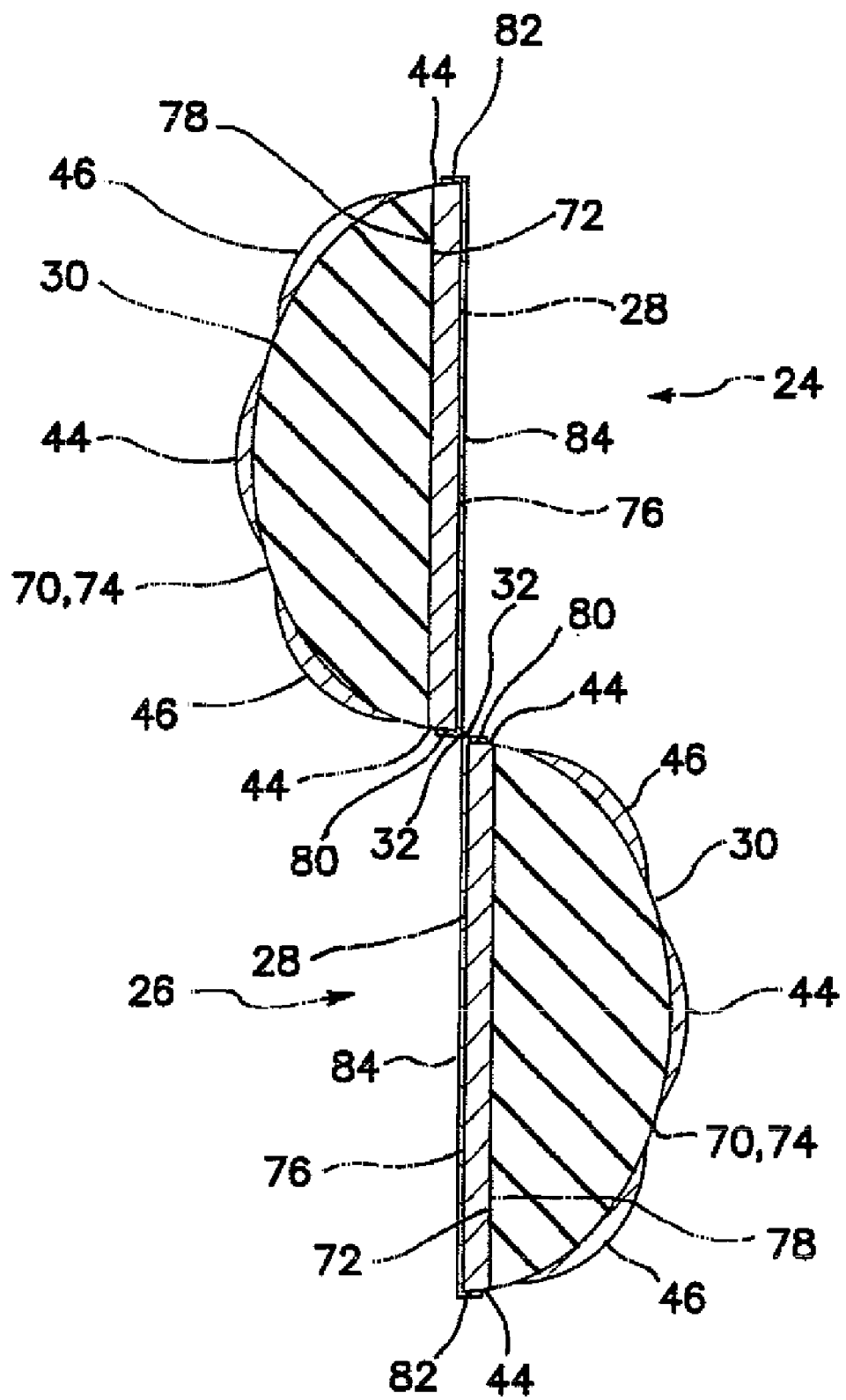
FIG. 12 is an end view, in cross-section, depicting the blades of the bipolar electrosurgical scissors with the electrodes being deposited onto an insulated body portion of the blades, similar to FIG. 8 but having additional electrodes on the shearing layer of the blades.

FIGS. 10-12 are similar to FIGS. 6-8, respectively Referring to FIGS. 10-12, the first and/or second scissor blade 24, 26 may include an insulating body with a shearing layer coupled to the insulating body. The first and second blades 24, 26 may include electrodes coupled to the insulating body (FIG. 10), electrodes inlayed into the insulating body (FIG. 11), electrodes deposited onto the insulating body (FIG. 12), or include suitable electrodes in any other form that is well known in the art positioned on the insulating body.

Similar to FIGS. 6-8, each of the first and second scissor blades 24, 26 of FIGS. 10-12 includes the insulating body 70 having the primary surface 72 corresponding with the shearing surface 28, and the secondary surface 74 corresponding with the opposed surface 30. The shearing layer 76 is coupled to the primary surface 72 of the insulating body 70. The shearing layer 76 includes the first, shearing surface 28, the second, opposed surface 78, and the cutting edge 32. The shearing layer 76 also includes the first and second edge surface 80, 82 with each of the edge surfaces including a first electrode 44. The first electrodes 44 on the first and second edge surfaces 80, 82 of the first scissor blade 24 are coupled to the first electrical connection 40 (FIG. 1) and the first electrodes 44 on the first and second edge surfaces 80, 82 of the second scissor blade 26 are coupled to the second electrical connection 42 (FIG. 1). The first edge surface 80 of the shearing layer 76 of each of the first and second blades 24, 26 coincides with the cutting edge 32 of the blades. The second, opposed surface 78 of the shearing layer 76 is coupled to the primary surface 72 of the insulating body 70.

With continued reference to FIGS. 10-12, as the shearing layer 76 includes the shearing surface 28 and cutting edge 32 of the blades 24, 26, the shearing layer is made of a material capable of forming a desirable cutting edge, such as a metallic material or other material that is well known in the art. With the shearing layer 76 of the first scissor blade 24 being coupled to the first electrical connection 40 (FIG. 1) and the shearing layer 76 of the second scissor blade 26 being coupled to the second electrical connection 42 (FIG. 1), it is necessary to electrically insulate the mating and interfacing portions of the shearing layer of each of the blades to prevent electrical shorting between the blades. Referring to FIGS. 10-12, the shearing surfaces 28 and cutting edges 32 of the shearing layers 76 of each of the first and second scissor blades 24, 26 may include an electrically insulating coating 84, such as a coating of amorphous diamond-like carbon or other suitable electrically insulating material that is well known in the art. On each of the first and second scissor blades 24, 26, portions of the first edge surface 80 and the second edge surface 82 proximate the shearing surface 28 are also coated with the electrically insulating coating 84. The portions of the first edge surface 80 and the second edge surface 82 that are proximate the second, opposed surface 78 of each of the first and second blades 24, 26 are not covered with the electrically insulating coating 84 and, thereby, function as first electrodes 44 for each of the blades. Alternatively, depending on selective uses for the scissors, the shearing layer 76 on each of the first and second blades 24, 26 may include a first electrode 44 on only one of the first and second edge surfaces 80, 82.

With further reference to FIGS. 10-12, the first scissor blade 24 may include at least one first electrode 44 and at least one second electrode 46 coupled to (FIG. 10), inlayed into (FIG. 11), or deposited onto (FIG. 12) the secondary surface 74 of the insulating body 70 of the first blade with the first and second electrodes positioned in an alternating relationship. The second scissor 26 blade may include at least one first electrode 44 and at least one second electrode 46 coupled to (FIG. 10), inlayed into (FIG. 11), or deposited onto (FIG. 12) the secondary surface 74 of the insulating body 70 of the second scissor blade with the first and second electrodes positioned in an alternating relationship and corresponding to the first and second electrodes on the first scissor blade. The electrically insulating material of which the insulating body 70 of the first and second scissor blades 24, 26 is formed has sufficient dielectric strength to substantially prevent electrical breakdown of the electrically insulating material.

On each of the first and second scissor blades 24, 26, the distance between the at least one first electrode 44 and the at least one second electrode 46 is sufficient to prevent electrical arcing between the electrodes. At the same time, the distance between the at least one first electrode 44 and the at least one second electrode 46 is small enough to permit simultaneous connection between the tissue 22 and two respective electrodes 44, 46 having opposing polarity (see FIG. 13). With the scissors 20 in a closed condition (FIG. 14), the distance between the first electrodes 44 on the first scissor blade 24 at the first and second edge surfaces 80, 82 and the first electrodes 44 on the second scissor blade 26 at the first and second edges 80, 82 is sufficient to prevent electrical arcing between the first electrodes on the first blade and the first electrodes on the second blade. At the same time, the distance between the first electrodes 44 on the first blade 24 and the first electrodes 44 on the second blade 26 is small enough to permit simultaneous connection between the tissue 22 and the first electrodes, which have opposing polarity, on adjacent edge surfaces 80, 82 of the shearing layers 76 of the first and second blades.

Figure 15:
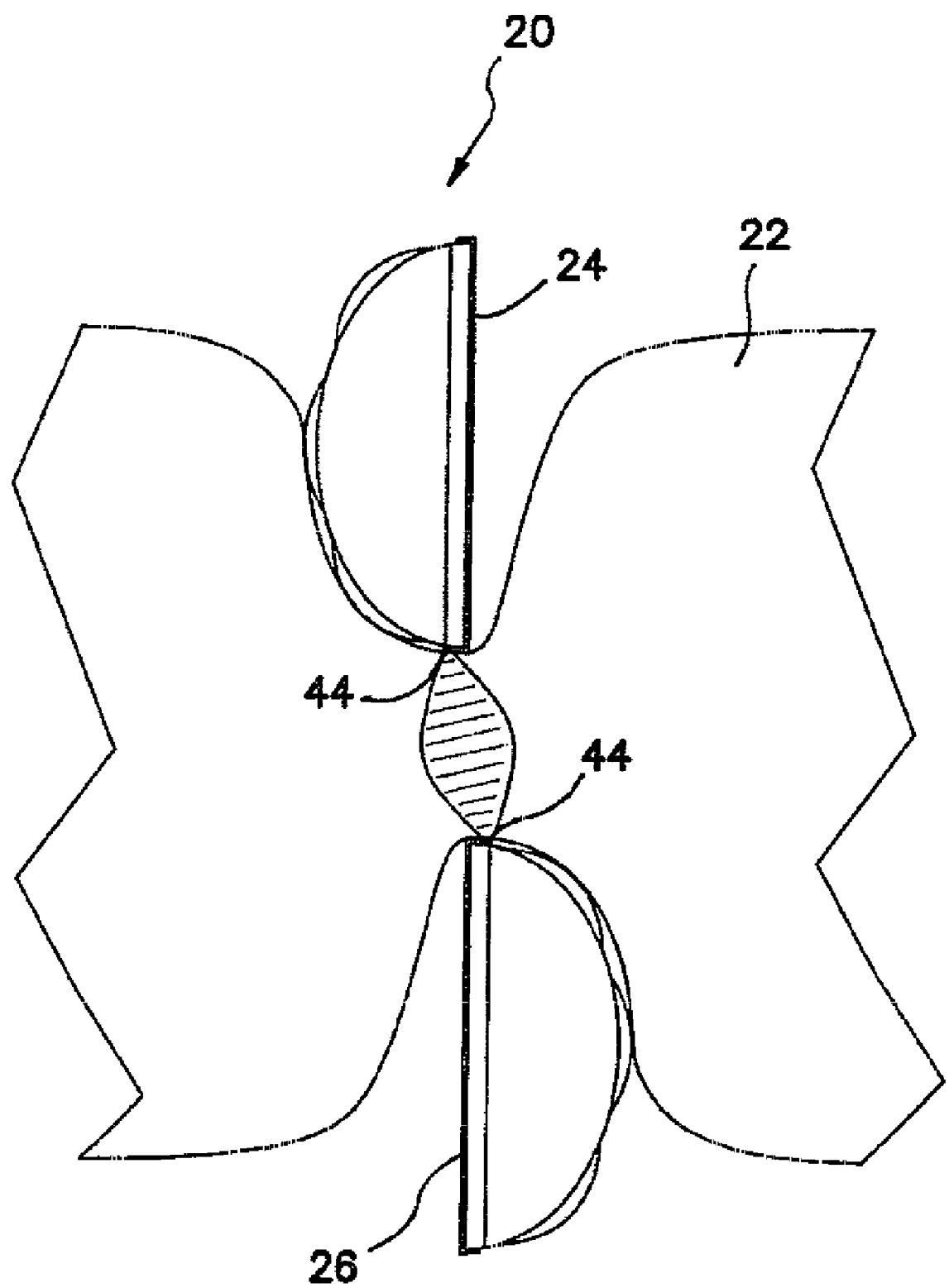
FIG. 15 is an end view of the blades of the bipolar electrosurgical scissors of FIG. 12 depicting the blades in an open condition with biological tissue positioned between the blades and the scissors energized in a first energized state with just the tissue between the blades being energized.

The bipolar electrosurgical scissors 20 of the present invention may be used for numerous surgical functions, including functions that have typically been reserved for monopolar surgical devices. For example, in the first energized state, as discussed above, the scissors 20 may be used to coagulate tissue 22 between the first and second scissor blades 24, 26 prior to mechanically cutting the tissue (see FIGS. 2 and 15). The scissors 20 are positioned in an open condition with the tissue 22 between the open blades 24, 26 In the first energized state, the first electrical connection 40 (FIG. 1) delivers electrical current only to the at least one first electrode 44 on the first scissor blade 24 and the second electrical connection 42 (FIG. 1) delivers electrical current only to the at least one first electrode 44 on the second scissor blade 26. The current travels mainly between the activated electrodes 44, thereby coagulating the tissue 22 between the open blades 24, 26 prior to the tissue being cut.

Figure 4:
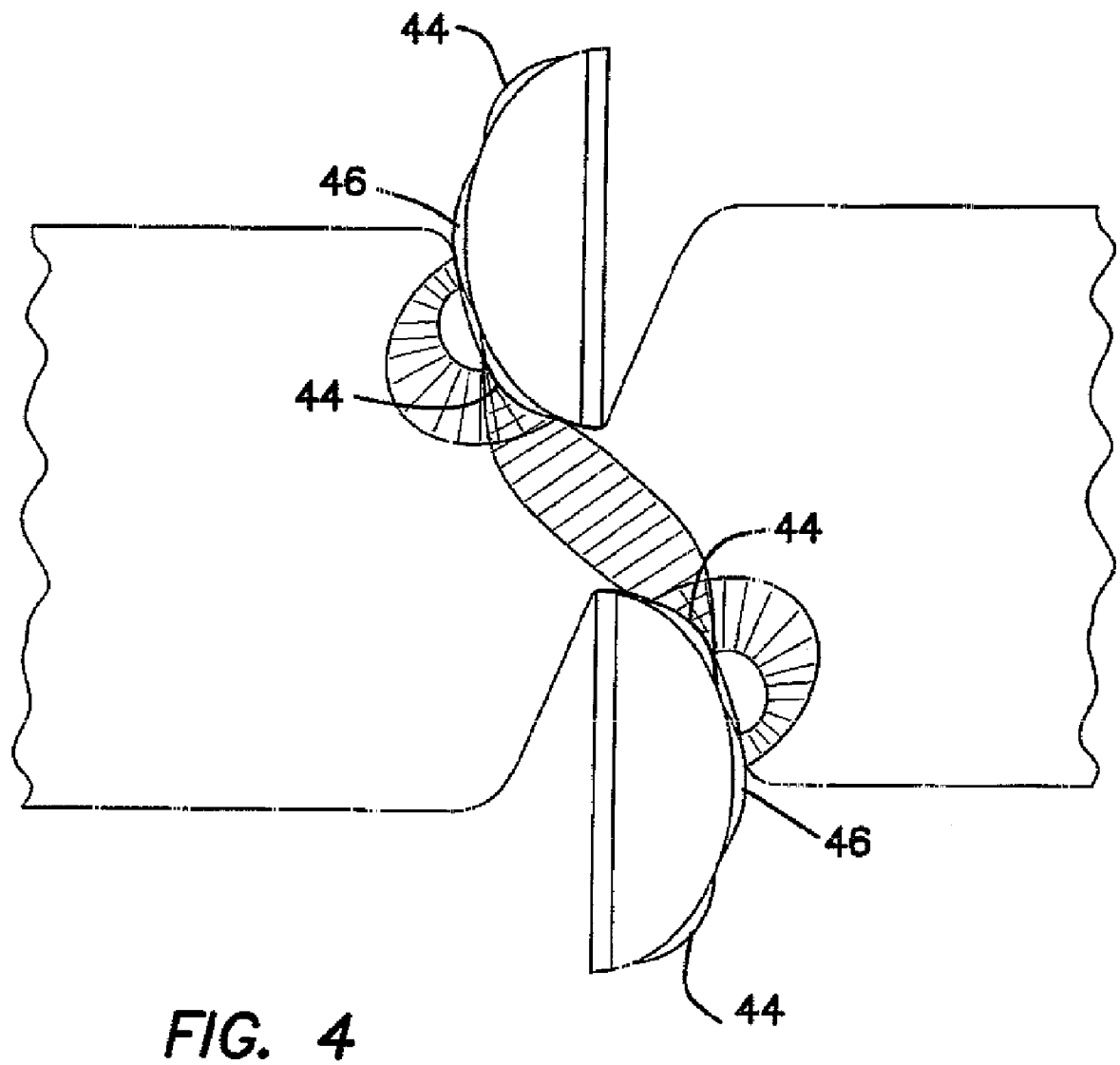
FIG. 4 is an end view of the blades of the bipolar electrosurgical scissors of FIG. 1 depicting the blades in an open condition with biological tissue positioned between the blades and the scissors energized in a second energized state with the tissue both between the blades and surrounding the blades being energized.
Figure 13:
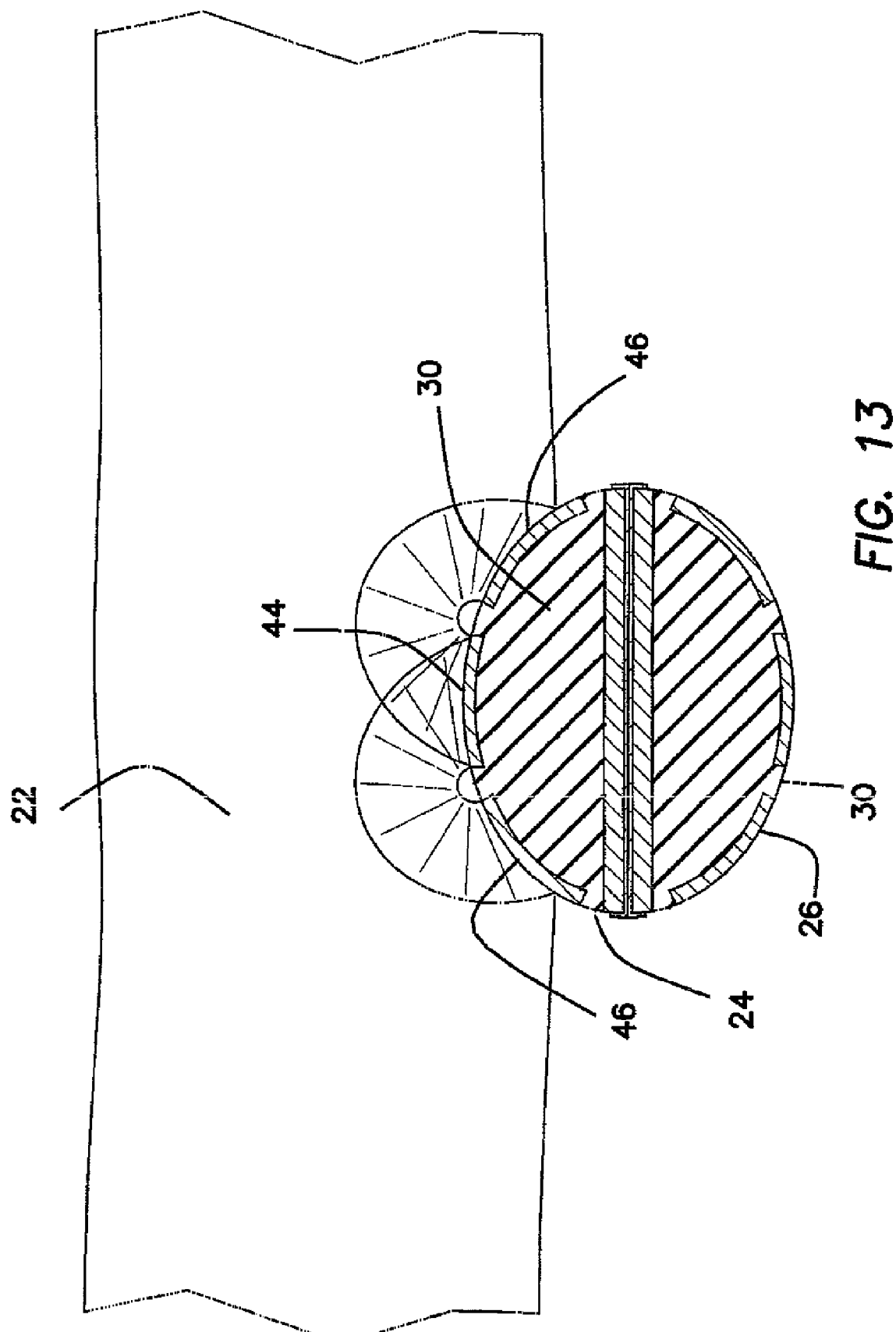
FIG. 13 is a side view depicting the electrosurgical scissors of FIG. 11 with the scissors energized in the second energized state to coagulate tissue with the side of the blade.
Figure 14:
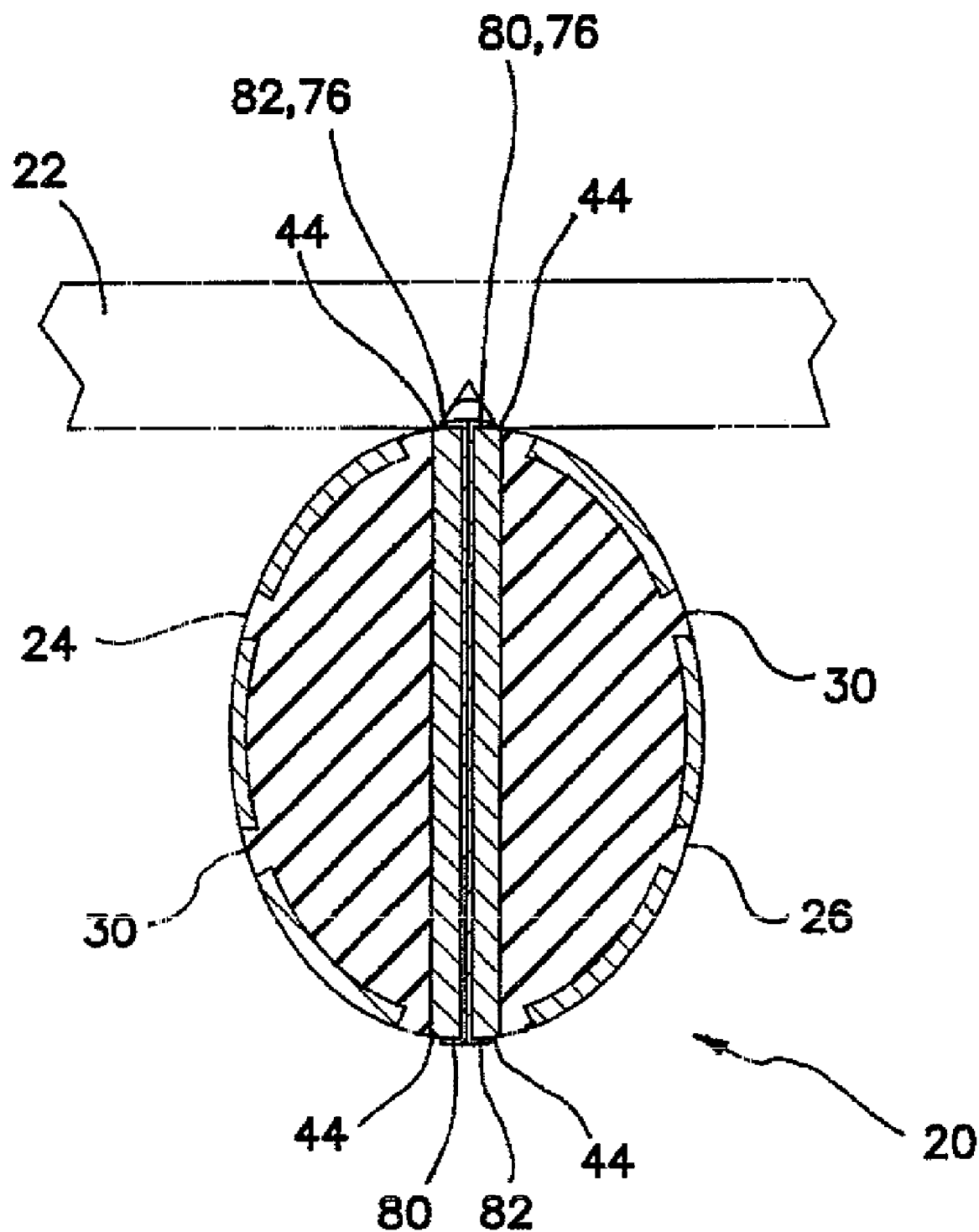
FIG. 14 is a side view depicting the electrosurgical scissors of FIG. 11 with the scissors energized in the second energized state to dissect tissue with the electrodes on the shearing layers of the blades.
Figure 16:
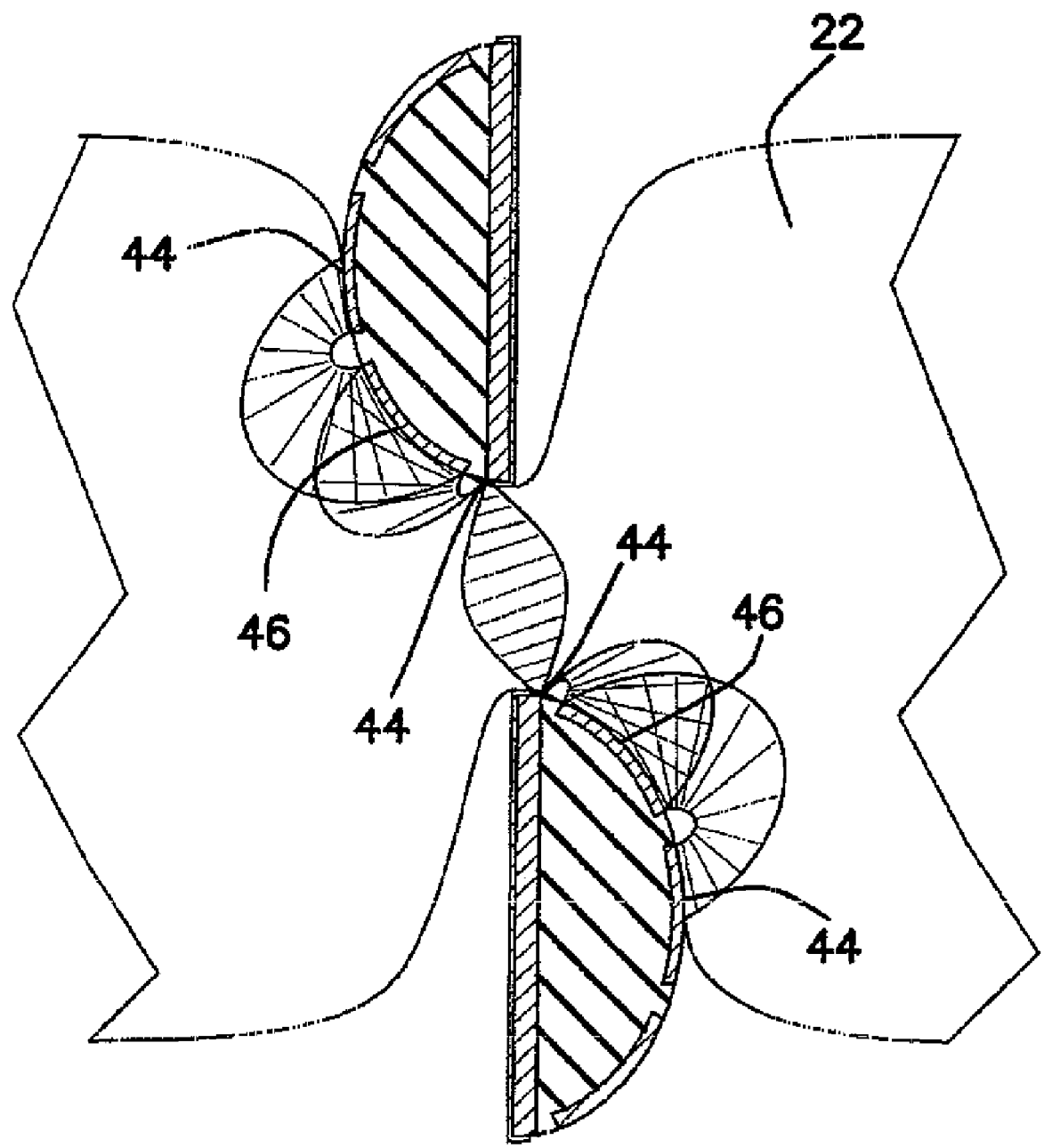
FIG. 16 is an end view of the blades of the bipolar electrosurgical scissors of FIG. 11 depicting the blades in an open condition with biological tissue positioned between the blades and the scissors energized in a second energized state with the tissue both between the blades and surrounding the blades being energized.
Figure 17:
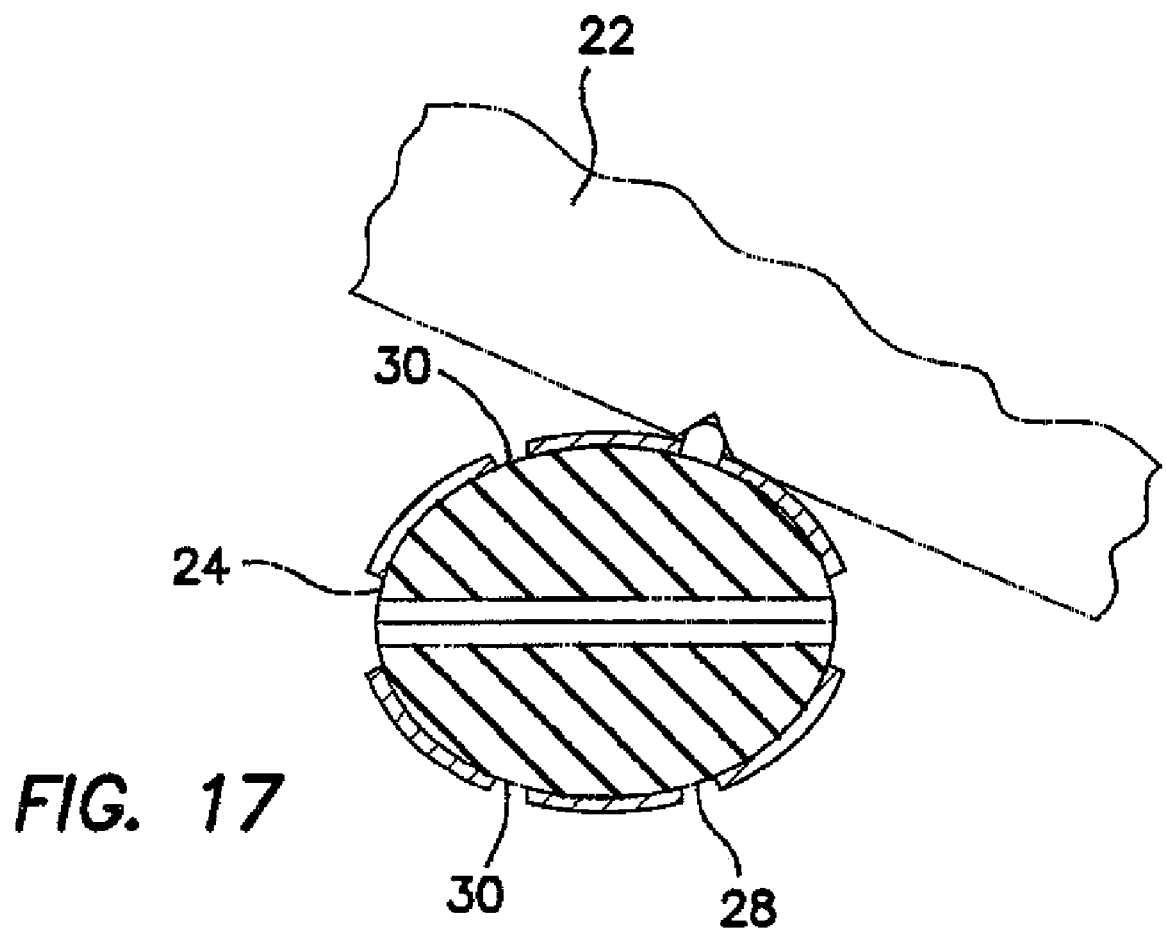
FIG. 17 is a side view depicting the electrosurgical scissors of FIG. 6 with the scissors energized in the second energized state to dissect tissue with the side of the blade.

Referring to FIGS. 4 and 16, in the second energized state, wherein all of the first and second electrodes 44, 46 on the first and second scissor blades 24, 26 are energized, the tissue 22 surrounding the tissue being mechanically cut is coagulated. In the second energized state, the tissue 22 being cut may also be coagulated in addition to coagulation of the tissue that is surrounding the tissue being cut. Referring to FIG. 13, in the second energized state the opposed surface 30 of one of the first and second scissor blades 24, 26 may be applied to tissue 22 to coagulate the tissue, similar to as is done with monopolar surgical devices. As stated above, the first and second electrodes 44, 46 are positioned such that each of a first and second electrode on one of the first and second scissor blades 24, 26 may be in contact with the tissue 22 at the same time. Referring to FIG. 14, in the first energized state with the scissors 20 in a closed condition, adjacent first electrodes on the edge surfaces 80, 82 of the shearing layers 76 of the first and second scissor blades 24, 26 may be moved across the tissue 22 in a sweeping motion to electrically dissect the tissue, similar to as is done with monopolar surgical devices. Alternatively, referring to FIG. 17, in the second energized state the opposed surface 30 of one of the first and second scissor blades 24, 26 may be moved across the tissue 22 in a sweeping motion to electrically dissect the tissue.

Although this invention has been disclosed with reference to certain structural configurations, it will be appreciated that these products are merely representative of many different embodiments of the invention. Accordingly, one is cautioned not to limit the concept only to the disclosed embodiments, but rather encouraged to determine the scope of the invention only with reference to the following claims.

The invention claimed is:

1. A bipolar electrosurgical scissors for use in treating biological tissue, comprising:
   a first scissor blade including a shearing surface, an opposed surface opposite the shearing surface, and a cutting edge, the shearing surface and cutting edge being electrically neutral;
   a second scissor blade pivotally coupled to the first blade, the second blade including a shearing surface, an opposed surface opposite the shearing surface, and a cutting edge, the shearing surface and cutting edge being electrically neutral;
   a first electrical connection for receiving an electrical current of a first polarity;
   a second electrical connection for receiving an electrical current of a second polarity, the second polarity being opposite the first polarity;
   at least one first electrode positioned on the opposed surface of the first scissor blade and coupled to the first electrical connection;
   at least one second electrode positioned on the opposed surface of the first scissor blade and coupled to the second electrical connection;
   at least one first electrode positioned on the opposed surface of the second scissor blade and coupled to the second electrical connection; and
   at least one second electrode positioned on the opposed surface of the second scissor blade and coupled to the first electrical connection,
   in a first energized state, the first electrical connection delivers electrical current only to the at least one first electrode on the first scissor blade and the second electrical connection delivers electrical current only to the at least one first electrode on the second scissor blade, and
   in a second energized state, the first electrical connection delivers electrical current to the at least one first electrode on the first scissor blade and to the at least one second electrode on the second scissor blade and the second electrical connection delivers electrical current to the at least one second electrode on the first scissor blade and to the at least one first electrode on the second scissor blade.

2. The bipolar electrosurgical scissors of claim 1, wherein the at least one first electrode on the opposed surface of the first scissor blade extends lengthwise along a length of the first scissor blade.

3. The bipolar electrosurgical scissors of claim 1, wherein:
   the distance between the at least one first electrode and the at least one second electrode on the opposed surface of the first scissor blade is sufficient to prevent electrical arcing between the electrodes, and small enough to permit simultaneous connection between the tissue and two respective electrodes having opposing polarity; and
   the distance between the at least one first electrode and the at least one second electrode on the opposed surface of the second scissor blade is sufficient to prevent electrical arcing between the electrodes, and small enough to permit simultaneous connection between the tissue and two respective electrodes having opposing polarity.

4. The bipolar electrosurgical scissors of claim 1, each of the first and second scissor blades comprising:
   an insulating body having a primary surface corresponding with the shearing surface of the blade and a secondary surface corresponding with the opposed surface of the blade;
   a shearing layer having a first, shearing surface, a second, opposed surface, and the cutting edge, the opposed surface of the shearing layer being coupled to the primary surface of the insulating body; and
   the at least one first electrode and the at least one second electrode being coupled to the secondary surface of the insulating body of each of the first and second scissor blades.

5. The bipolar electrosurgical scissors of claim 4, wherein the first and second electrodes are positioned in an alternating relationship with the first and second electrodes on the second scissor blade corresponding with the first and second electrodes on the first scissor blade.

6. The bipolar electrosurgical scissors of claim 4, wherein a material forming the electrically insulating body of the first and second scissor blades has sufficient dielectric strength to substantially prevent electrical breakdown of the electrically insulating body.

7. The bipolar electrosurgical scissors of claim 1, wherein the first scissor blade further comprises a third electrode positioned adjacent the shearing surface, the third electrode coupled to the first electrical connection, and wherein the shearing surface is formed of an electrically insulating coating; and
   wherein the second scissor blade further comprises a third electrode positioned adjacent the shearing surface, the third electrode coupled to the second electrical connection, and wherein the shearing surface is formed of an electrically insulating coating.

8. A bipolar electrosurgical scissors for use in treating biological tissue, comprising:

a first scissor blade including a shearing surface, an opposed surface opposite the shearing surface, and a cutting edge, the shearing surface and cutting edge of the first scissor blade being electrically neutral; and a second scissor blade pivotally coupled to the first scissor blade, the second scissor blade including a shearing surface, an opposed surface opposite the shearing surface, and a cutting edge, the shearing surface and cutting edge of the second scissor blade being electrically neutral, the shearing surface of the second scissor blade facing the shearing surface of the first scissor blade and interfacing with the shearing surface of the first scissor blade;

each of the first and second scissor blades including a laminated structure comprising:
  a first layer coinciding with the shearing surface and cutting edge of the scissor blade, the first layer including a first surface and a second, opposed surface opposite the first surface, the first surface of the first layer forming the shearing surface of the blade;
  a second layer coupled to the second surface of the first layer, the second layer being electrically nonconductive,
  a third layer coupled to the second layer on the side opposite the first layer with the second layer completely separating the third layer from the first layer, the third layer being electrically conductive and forming at least one first electrode at exposed portions thereof,
  a fourth layer coupled to the third layer on the side opposite the second layer, the fourth layer being electrically nonconductive, and
  a fifth layer coupled to the fourth layer on the side opposite the third layer with the fourth layer completely separating the fifth layer from the third layer, the fifth layer being electrically conductive and forming at least one second electrode at exposed portions thereof.

9. The bipolar electrosurgical scissors of claim 8, further comprising:
  a first electrical connection for receiving an electrical current of a first polarity; and
  a second electrical connection for receiving an electrical current of a second polarity, the second polarity being opposite the first polarity; and
  wherein the first electrical connection is coupled to the at least one first electrode on the first scissor blade and to the at least one second electrode on the second scissor blade; and
  wherein the second electrical connection is coupled to the at least one second electrode on the first scissor blade and to the at least one first electrode on the second scissor blade.

10. The bipolar electrosurgical scissors of claim 9, wherein in a first energized state, the first electrical connection delivers electrical current only to the at least one first electrode on the first scissor blade and the second electrical connection delivers electrical current only to the at least one first electrode on the second scissor blade; and
  wherein in a second energized state, the first electrical connection delivers electrical current to the at least one first electrode on the first scissor blade and to the at least one second electrode on the second scissor blade and the second electrical connection delivers electrical current to the at least one second electrode on the first scissor blade and to the at least one first electrode on the second scissor blade.

11. The bipolar electrosurgical scissors of claim 9, wherein the first layer of the first scissor blade is electrically neutral, and wherein the first layer of the second scissor blade is electrically neutral.

12. The bipolar electrosurgical scissors of claim 8, further comprising an electrically insulating coating disposed on the first surface of the first layer of each of the first and second scissor blades.

13. The bipolar electrosurgical scissors of claim 12, wherein the first layer of each of the first and second scissor blades is electrically conductive and forms at least one third electrode at exposed portions thereof.

14. The bipolar electrosurgical scissors of claim 13, further comprising a first electrical connection for receiving an electrical current of a first polarity; and
  a second electrical connection for receiving an electrical current of a second polarity, the second polarity being opposite the first polarity; and
  wherein the first electrical connection is coupled to the at least one first electrode on the first scissor blade, to the at least one third electrode on the first scissor blade, and to the at least one second electrode on the second scissor blade; and
  wherein the second electrical connection is coupled to the at least one second electrode on the first scissor blade, to the at least one first electrode on the second scissor blade, and to the at least one third electrode on the second scissor blade.

15. The bipolar electrosurgical scissors of claim 14, wherein in a first energized state, the first electrical connection delivers electrical current only to the at least one third electrode on the first scissor blade and the second electrical connection delivers electrical current only to the at least one third electrode on the second scissor blade.

16. A bipolar electrosurgical scissors for use in treating biological tissue, comprising:
  a first scissor blade having a shearing surface, and an opposed surface opposite the shearing surface, the first scissor blade comprising:
    at least one first electrode positioned on the opposed surface; and
    at least one second electrode positioned on the opposed surface;
  a second scissor blade pivotally coupled to the first scissor blade by a pivot pin, the second scissor blade having a shearing surface and an opposed surface opposite the shearing surface, the second scissor blade comprising:
    at least one first electrode positioned on the opposed surface; and
    at least one second electrode positioned on the opposed surface; and
  wherein in a first energized state, electrical current of a first polarity is delivered only to the at least one first electrode on the first scissor blade and electrical current of a second polarity opposite the first polarity is delivered only to the at least one first electrode on the second scissor blade, and
  in a second energized state, electrical current of the first polarity is delivered to the at least one first electrode on the first scissor blade and to the at least one second electrode on the second scissor blade and electrical current of the second polarity is delivered to the at least one second electrode on the first scissor blade and to the at least one first electrode on the second scissor blade.

17. The bipolar electrosurgical scissors of claim 16, wherein the shearing surfaces of the first scissor blade and the second scissor blade are electrically neutral.

18. The bipolar electrosurgical scissors of claim 16, wherein the shearing surfaces of the first scissor blade and the second scissor blade each comprise an electrically insulating coating.

19. The bipolar electrosurgical scissors of claim 16, wherein the first scissor blade is formed of a laminated construction comprising a plurality of layers, and wherein the second scissor blade is formed of a laminated construction comprising a plurality of layers.

20. The bipolar electrosurgical scissors of claim 16, wherein the first scissor blade further comprises an insulating body having a primary surface corresponding with the shearing surface of the blade and a secondary surface corresponding with the opposed surface of the blade.

21. The bipolar electrosurgical scissors of claim 16, wherein the first scissor blade comprises two first electrodes and one second electrode.

\* \* \* \* \*